(12) United States Patent  
Khubani et al.

(10) Patent No.: US 11,759,227 B2  
(45) Date of Patent: Sep. 19, 2023

(54) DERMAPLANING DEVICE AND RELATED SYSTEM

(71) Applicant: Church & Dwight Co., Inc., Princeton, NJ (US)

(72) Inventors: Anand Khubani, Morristown, NJ (US); David Stowers, Morristown, NJ (US); Hayley Matarazzo, Morristown, NJ (US); Eric Langberg, Milford, PA (US); Emil Braca, Riverdale, NJ (US); Aaron Szymanski, Thomaston, CT (US)

(73) Assignee: Church & Dwight Co., Inc., Princeton, NJ (US)

( * ) Notice: Subject to any disclaimer, the term of this patent is extended or adjusted under 35 U.S.C. 154(b) by 0 days.

(21) Appl. No.: 16/791,703

(22) Filed: Feb. 14, 2020

(65) Prior Publication Data

US 2020/0261109 A1 Aug. 20, 2020

Related U.S. Application Data

(60) Provisional application No. 62/882,747, filed on Aug. 5, 2019, provisional application No. 62/806,610, filed on Feb. 15, 2019.

(51) Int. Cl.
*A61B 17/32* (2006.01)
*A61B 17/54* (2006.01)
*A61B 17/00* (2006.01)

(52) U.S. Cl.
CPC ...... *A61B 17/320068* (2013.01); *A61B 17/54* (2013.01); *A61B 2017/00761* (2013.01);
(Continued)

(58) Field of Classification Search
CPC  A61B 17/320068; A61B 2017/320074; A61B 2017/320075; A61B 2017/00761; A61B 2017/00907; A61B 17/54; A61B 17/32; A61B 17/3209; A61B 17/32093; A61B 17/3211; A61B 17/3213;
(Continued)

(56) References Cited

U.S. PATENT DOCUMENTS

| 917,043 A | 4/1909 | Gage |
| 1,003,749 A | 9/1911 | Jaennert |

(Continued)

FOREIGN PATENT DOCUMENTS

| AU | 363308 S | 8/2015 |
| CA | 2514852 C | 11/2011 |

(Continued)

*Primary Examiner* — Dianne Dornbusch
(74) *Attorney, Agent, or Firm* — Womble Bond Dickinson (US) LLP

(57) ABSTRACT

A dermaplaning device and related system are disclosed. The dermaplaning device may include a longitudinally-extending handle having a first end defining a longitudinally-extending recess and an opposing second end. The dermaplaning device may further include a blade assembly having a top side engageable with the recess of the handle and an opposing bottom side including a blade with a cutting edge. The dermaplaning device may further include a lighting arrangement provided about the first end of the handle to illuminate at least a portion of the blade assembly engaged with the recess.

15 Claims, 22 Drawing Sheets

(52) U.S. Cl.
CPC .............. *A61B 2017/00907* (2013.01); *A61B 2017/320075* (2017.08)

(58) Field of Classification Search
CPC  A61B 2017/00747; A61B 2017/00752; A61B 2017/00769; A61B 2017/00774; A61B 2017/320004; A61B 2017/320008; A61B 2017/320012; A61B 2017/320052; A61B 2017/32113; A61B 2017/00756
See application file for complete search history.

(56) References Cited

U.S. PATENT DOCUMENTS

| | | |
|---|---|---|
| 1,035,548 A | 8/1912 | Dickenson |
| 1,579,577 A | 4/1926 | Thompson |
| 1,823,808 A | 9/1931 | Thompson |
| 1,852,362 A | 4/1932 | Newby |
| 2,306,890 A | 12/1942 | Mayeux |
| 3,263,328 A | 8/1966 | Craig |
| 3,263,330 A | 8/1966 | Ferrara |
| 3,392,446 A | 7/1968 | Ferrara |
| 3,505,734 A | 4/1970 | Iten |
| 3,555,682 A | 1/1971 | Laszlo |
| 3,600,804 A | 8/1971 | Brown |
| 3,606,006 A | 9/1971 | Raybois |
| 3,675,325 A | 7/1972 | Michelson |
| 3,685,150 A * | 8/1972 | Risher .................... B26B 21/18 30/74.1 |
| 3,750,285 A | 8/1973 | Michelson |
| 3,815,227 A | 6/1974 | Hood |
| 3,835,532 A | 9/1974 | Petrillo |
| 3,854,201 A | 12/1974 | Dawidowicz et al. |
| 4,037,322 A * | 7/1977 | Bresler .................. B26B 21/10 30/53 |
| 4,094,066 A | 6/1978 | Daniel, Jr. |
| 4,106,620 A | 8/1978 | Brimmer et al. |
| 4,173,285 A | 11/1979 | Kiraly et al. |
| D254,692 S | 4/1980 | Del Re |
| 4,341,305 A | 7/1982 | Schultz |
| D276,751 S | 12/1984 | Kahn |
| 4,542,741 A | 9/1985 | Burgin |
| 4,622,742 A | 11/1986 | Lee |
| 4,700,477 A | 10/1987 | Heller |
| 4,742,909 A | 5/1988 | Apptille, Jr. et al. |
| D298,576 S | 11/1988 | Iten |
| 4,845,845 A | 7/1989 | Scott |
| 4,912,846 A | 4/1990 | Yu |
| 4,914,817 A | 4/1990 | Galligan et al. |
| D311,971 S | 11/1990 | Faerber |
| D318,143 S | 7/1991 | Wieneke |
| 5,348,152 A | 9/1994 | Kiyoshi et al. |
| D351,485 S | 10/1994 | Miskin |
| D361,637 S | 8/1995 | Miskin |
| 5,518,114 A | 5/1996 | Kohring et al. |
| 5,560,105 A | 10/1996 | Ichiyanagi |
| 5,636,442 A | 6/1997 | Wain |
| D400,301 S | 10/1998 | Wong |
| 5,908,036 A * | 6/1999 | Andrews ................ B26B 21/10 132/215 |
| 5,979,056 A * | 11/1999 | Andrews ................ B26B 21/00 30/356 |
| 6,067,714 A | 5/2000 | Taylor et al. |
| D427,376 S | 6/2000 | Scott |
| 6,164,290 A * | 12/2000 | Andrews ................ A45D 24/36 132/215 |
| 6,434,828 B1 | 8/2002 | Andrews |
| 6,530,151 B2 | 3/2003 | Kameka |
| D485,013 S | 1/2004 | Leventhal et al. |
| 6,701,619 B2 | 3/2004 | Haruyuki |
| D488,260 S | 4/2004 | Khubani |
| 6,722,039 B2 | 4/2004 | Kitano |
| D497,035 S | 10/2004 | Khubani |
| D499,511 S | 12/2004 | Wakayama |
| D509,026 S | 8/2005 | Leventhal et al. |
| D513,092 S | 12/2005 | Ajootian |
| 7,028,405 B2 | 4/2006 | Paas et al. |
| D531,358 S | 10/2006 | Lee |
| D531,754 S | 11/2006 | Lee |
| D532,157 S | 11/2006 | Lee |
| 7,172,069 B2 | 2/2007 | Coffin et al. |
| D541,985 S | 5/2007 | Peña |
| D541,987 S | 5/2007 | Sugawara |
| D542,468 S | 5/2007 | Stiles |
| 7,251,896 B2 | 8/2007 | Khubani |
| D552,794 S | 10/2007 | Klein |
| D553,295 S | 10/2007 | Khubani |
| D554,291 S | 10/2007 | Darnell et al. |
| D561,941 S | 2/2008 | Khubani |
| D569,552 S | 5/2008 | Marquez |
| D578,708 S | 10/2008 | Ringart et al. |
| 7,441,336 B2 | 10/2008 | Hawes et al. |
| 7,637,265 B2 | 12/2009 | Funatsu et al. |
| D612,420 S | 3/2010 | Suero, Jr. et al. |
| D620,644 S | 7/2010 | Lau et al. |
| 7,757,404 B2 | 7/2010 | Ouchi et al. |
| D627,102 S | 11/2010 | Leventhal et al. |
| D634,067 S | 3/2011 | Stowers et al. |
| D634,068 S | 3/2011 | Stowers et al. |
| D636,531 S | 4/2011 | Wilson |
| 8,061,041 B2 | 11/2011 | Jessemey et al. |
| D663,483 S | 7/2012 | Lee |
| D674,145 S | 1/2013 | Ino |
| D674,558 S | 1/2013 | Ino |
| D676,196 S | 2/2013 | Gaugler |
| 8,563,904 B2 | 10/2013 | Cho |
| 8,615,886 B1 | 12/2013 | Childers |
| D728,159 S | 4/2015 | Szymanski |
| D728,160 S | 4/2015 | Szymanski |
| D748,859 S | 2/2016 | Boulanger |
| D750,323 S | 2/2016 | Exley |
| D758,663 S | 6/2016 | Van Maanen |
| D763,506 S | 8/2016 | Barrett |
| D776,877 S | 1/2017 | Zadro |
| D781,496 S | 3/2017 | Butler et al. |
| D788,850 S | 6/2017 | Timm et al. |
| D799,752 S | 10/2017 | Mori |
| D822,279 S | 7/2018 | Newman |
| D830,632 S | 10/2018 | Hage et al. |
| D831,274 S | 10/2018 | Gamble et al. |
| 10,111,681 B2 | 10/2018 | Levy |
| D834,253 S | 11/2018 | Khubani et al. |
| D834,254 S | 11/2018 | Khubani et al. |
| D836,839 S | 12/2018 | Guo |
| D836,840 S | 12/2018 | Khubani et al. |
| D838,040 S | 1/2019 | Mayberry |
| D841,242 S | 2/2019 | Marut |
| D841,247 S | 2/2019 | Stowers |
| D841,886 S | 2/2019 | Brormann |
| D841,887 S | 2/2019 | Stowers |
| D842,541 S | 3/2019 | Brormann |
| 10,300,619 B2 | 5/2019 | Khubani et al. |
| D857,296 S | 8/2019 | Khubani et al. |
| D857,297 S | 8/2019 | Khubani et al. |
| D860,535 S | 9/2019 | Weaver |
| D868,373 S | 11/2019 | Kling et al. |
| 10,543,606 B2 | 1/2020 | Schatz |
| D888,341 S | 6/2020 | Stowers |
| D889,039 S | 6/2020 | Stowers |
| D890,996 S | 7/2020 | Baratelli et al. |
| D891,699 S | 7/2020 | Baratelli et al. |
| D891,700 S | 7/2020 | Baratelli et al. |
| D891,701 S | 7/2020 | Baratelli et al. |
| D891,703 S | 7/2020 | Baratelli et al. |
| D893,101 S | 8/2020 | Szymanski |
| D894,489 S | 8/2020 | Baratelli et al. |
| D894,490 S | 8/2020 | Baratelli et al. |
| D894,491 S | 8/2020 | Baratelli et al. |
| D894,492 S | 8/2020 | Baratelli et al. |
| D894,493 S | 8/2020 | Baratelli et al. |
| D898,283 S | 10/2020 | Stowers |
| D907,851 S | 1/2021 | Lombardo et al. |
| D907,853 S | 1/2021 | Bessho |
| 2005/0262694 A1 | 12/2005 | Ouchi et al. |

(56) References Cited

U.S. PATENT DOCUMENTS

| | | | |
|---|---|---|---|
| 2005/0262696 | A1 | 12/2005 | Ouchi et al. |
| 2006/0130334 | A1 | 6/2006 | Park |
| 2006/0156551 | A1 | 7/2006 | Khubani et al. |
| 2012/0101512 | A1 | 4/2012 | Locke et al. |
| 2013/0042481 | A1* | 2/2013 | Lombardo ............. B26B 19/46 30/34.05 |
| 2013/0247393 | A1 | 9/2013 | Poladian |
| 2014/0366387 | A1 | 12/2014 | Schuft |
| 2015/0073438 | A1 | 3/2015 | Levy |
| 2016/0166273 | A1* | 6/2016 | Levy ............... A45D 26/0004 606/131 |
| 2017/0042568 | A1* | 2/2017 | Levy ............... A45D 26/0004 |
| 2017/0333071 | A9 | 11/2017 | Levy |
| 2018/0256192 | A1 | 9/2018 | Levy |
| 2019/0320778 | A1 | 10/2019 | Moon |
| 2020/0055206 | A1 | 2/2020 | Teteak et al. |
| 2020/0094427 | A1 | 3/2020 | Barrett et al. |
| 2020/0331159 | A1 | 10/2020 | Yoo |
| 2021/0170613 | A1 | 6/2021 | Teteak et al. |

FOREIGN PATENT DOCUMENTS

| | | |
|---|---|---|
| CA | 163071 S | 4/2016 |
| CN | 1701934 | 11/2005 |
| CN | 302831231 | 5/2014 |
| CN | 302933266 | 9/2014 |
| CN | 303417664 | 10/2015 |
| CN | 206287178 | 6/2017 |
| CN | 304310019 | 10/2017 |
| CN | 304316262 | 10/2017 |
| CN | 207888697 | 9/2018 |
| CN | 304977093 | 1/2019 |
| CN | 305077826 | 3/2019 |
| CN | 305449692 | 11/2019 |
| CN | 306152195 | 11/2020 |
| CN | 306733932 | 8/2021 |
| CN | 306755343 | 8/2021 |
| DE | 402017203423-0003 | 12/2017 |
| EM | 000706536-0001 | 4/2007 |
| EM | 000706536-0002 | 4/2007 |
| EM | 007978788-0001 | 6/2020 |
| GB | 6056436 | 3/2019 |
| GB | 6057286 | 3/2019 |
| GB | 6062610 | 6/2019 |
| GB | 6062614 | 6/2019 |
| JP | D1312712 | 9/2007 |
| JP | D1562084 | 9/2016 |
| JP | D1562085 | 9/2016 |
| JP | D1671942 | 10/2020 |
| JP | D1672687 | 10/2020 |
| JP | D1676744 | 12/2020 |
| KR | 10-0613983 B1 | 8/2006 |
| PE | 001405-2019 | 3/2020 |

* cited by examiner

DERMAPLANING DEVICE AND RELATED SYSTEM

CROSS-REFERENCE TO RELATED APPLICATIONS

This application claims priority to U.S. Provisional Application No. 62/882,747, filed on Aug. 5, 2019 and entitled, "Dermaplaning System and Related Methods of Assembly," and U.S. Provisional Application No. 62/806,610, filed on Feb. 15, 2019 and entitled "Dermaplaning Device," and claims priority to each of these applications being incorporated by reference herein.

FIELD OF THE DISCLOSURE

The invention relates to a dermaplaning device and related system. More particularly, this invention allows users to safely and effectively scrape the epidermis of their skin to create a variety of cosmetic benefits for the skin. Dermaplaning helps to smooth skin, exfoliate the skin, reduce the appearance of wrinkles and scars, promotes the productions of collagen and elastin, and to clean the skin.

BACKGROUND

Various processes are known for treating facial skin. These processes are known to include hand-held devices and fall into several categories as follows: shaving, cleansing and moisturizing, dermabrasion, dermaplaning (exfoliation), and debridement. Of these categories, dermaplaning is a relatively popular process that is relatively simple and safe and is used for exfoliating the epidermis, i.e., an outer layer of cells in the skin, and removing fine vellus hair, i.e., "peach fuzz," from the skin. Dermaplaning is a process normally performed by licensed skin care professionals, such as estheticians, because of the use of a surgical scalpel or similar blade to exfoliate the epidermis. Using a scalpel and a delicate touch, the scalpel is swept across the skin with light feathering strokes to exfoliate the skin to remove the oldest dead skin cells on the skin's outermost surface. Such scalpels are not available for non-professional use. As such, dermaplaning is only available at spas with licensed skin care professionals. Such dermaplaning treatments at spas can be relatively expensive.

Dermaplaning facial skin has many benefits. For example, removing epidermal skin allows skin care products to penetrate more readily into deeper layers of the skin for better results. As mentioned above, dermaplaning removes vellus hair which tends to cause a build-up of dirt and oils in the follicles. Removal of the hair results in healthier looking skin. Unfortunately, there are no known dermaplaning devices known for non-professional home use.

Accordingly, there exists a need for a dermaplaning device and related system that addresses or solves at least the issues mentioned herein.

BRIEF SUMMARY OF THE DISCLOSURE

The present disclosure relates to a dermaplaning device and related system which advantageously reduces the problems associated with conventional dermaplaning devices and systems.

The present disclosure thus includes, without limitation, the following embodiments:

A dermaplaning device comprising a longitudinally-extending handle having a first end defining a longitudinally-extending recess and an opposing second end; a blade assembly having a top side engageable with the recess of the handle and an opposing bottom side comprising a blade with a cutting edge; and a lighting arrangement provided about the first end of the handle to illuminate at least a portion of the blade assembly engaged with the recess.

The dermaplaning device of any preceding embodiment or any combination of preceding embodiments, wherein the lighting arrangement comprises a light source and a power source in electric communication with the light source.

The dermaplaning device of any preceding embodiment or any combination of preceding embodiments, the dermaplaning device further comprising a switch in electric communication with the power source, the switch being arranged to activate the power source and thereby illuminate at least a portion of the blade assembly when actuated.

The dermaplaning device of any preceding embodiment or any combination of preceding embodiments, wherein the blade assembly comprises a translucent material such that light from the light source passes through the translucent material of the blade assembly so as to illuminate at least a portion of the blade assembly and thereby a target area during use of the dermaplaning device.

The dermaplaning device of any preceding embodiment or any combination of preceding embodiments, wherein the light source is arranged on the first end of the handle and adjacent to the recess.

The dermaplaning device of any preceding embodiment or any combination of preceding embodiments, wherein the second end of the handle defines an internal compartment arranged to contain the power source.

The dermaplaning device of any preceding embodiment or any combination of preceding embodiments, the dermaplaning device further comprising a motor in electric communication with the power source and the blade, wherein the motor is configured to cause one or both of vibration and reciprocation of the blade upon actuation of the motor.

The dermaplaning device of any preceding embodiment or any combination of preceding embodiments, wherein the blade assembly is attachable to and removable from the first end of the handle.

The dermaplaning device of any preceding embodiment or any combination of preceding embodiments, the dermaplaning device further comprising a cover arrangeable about the first end of the handle so as to enclose at least the cutting edge of the blade.

The dermaplaning device of any preceding embodiment or any combination of preceding embodiments, wherein the blade assembly and the handle are engageable by magnets, a press fit, a snap fit, a twist lock, a biased lock, or combinations thereof.

The dermaplaning device of any preceding embodiment or any combination of preceding embodiments, wherein a safety guard is arranged over the cutting edge of the blade so as to limit a cutting depth of the blade.

The dermaplaning device of any preceding embodiment or any combination of preceding embodiments, the dermaplaning device further comprising an engagement mechanism disposed on the handle, wherein actuation of the engagement mechanism releases the blade assembly including the blade from engagement with the recess of the handle.

The dermaplaning device of any preceding embodiment or any combination of preceding embodiments, wherein the first end of the handle defining the recess is longitudinally offset from the opposing second end of the handle.

The dermaplaning device of any preceding embodiment or any combination of preceding embodiments, wherein the second end of the handle comprises a gripping region for a user to grip the dermaplaning device during use.

A dermaplaning system comprising: a dermaplaning device comprising: a longitudinally-extending handle having a first end defining a longitudinally-extending recess and an opposing second end; a blade assembly having a top side engageable with the recess of the handle and an opposing bottom side comprising a blade with a cutting edge; and a lighting arrangement provided about the first end of the handle to illuminate at least a portion of the blade assembly engaged with the recess; and a blade dispenser defining a plurality of cavities, each cavity being arranged to retain a blade therein and dispense the blade upon engagement of the top side of the blade with the recess of the dermaplaning device.

The dermaplaning system of any preceding embodiment or any combination of preceding embodiments, wherein the lighting arrangement comprises a light source and a power source in electric communication with the light source.

The dermaplaning system of any preceding embodiment or any combination of preceding embodiments, wherein the dermaplaning device comprises a switch in electric communication with the power source, the switch being arranged to activate the power source and thereby illuminate at least a portion of the blade assembly when actuated.

The dermaplaning system of any preceding embodiment or any combination of preceding embodiments, wherein the blade assembly comprises a translucent material such that light from the light source passes through the translucent material of the blade assembly so as to illuminate at least a portion of the blade assembly and thereby a target area during use of the dermaplaning device.

The dermaplaning system of any preceding embodiment or any combination of preceding embodiments, wherein the light source is arranged on the first end of the handle and adjacent to the recess.

The dermaplaning system of any preceding embodiment or any combination of preceding embodiments, wherein the dermaplaning device comprises a motor in electric communication with the power source and the blade, wherein the motor is configured to cause one or both of vibration and reciprocation of the blade upon actuation of the motor.

These and other features, aspects, and advantages of the present disclosure will be apparent from a reading of the following detailed description together with the accompanying drawings, which are briefly described below. The present disclosure includes any combination of two, three, four, or more features or elements set forth in this disclosure or recited in any one or more of the claims, regardless of whether such features or elements are expressly combined or otherwise recited in a specific embodiment description or claim herein. This disclosure is intended to be read holistically such that any separable features or elements of the disclosure, in any of its aspects and embodiments, should be viewed as intended to be combinable, unless the context of the disclosure clearly dictates otherwise.

BRIEF DESCRIPTION OF THE DRAWINGS

Figure 1:
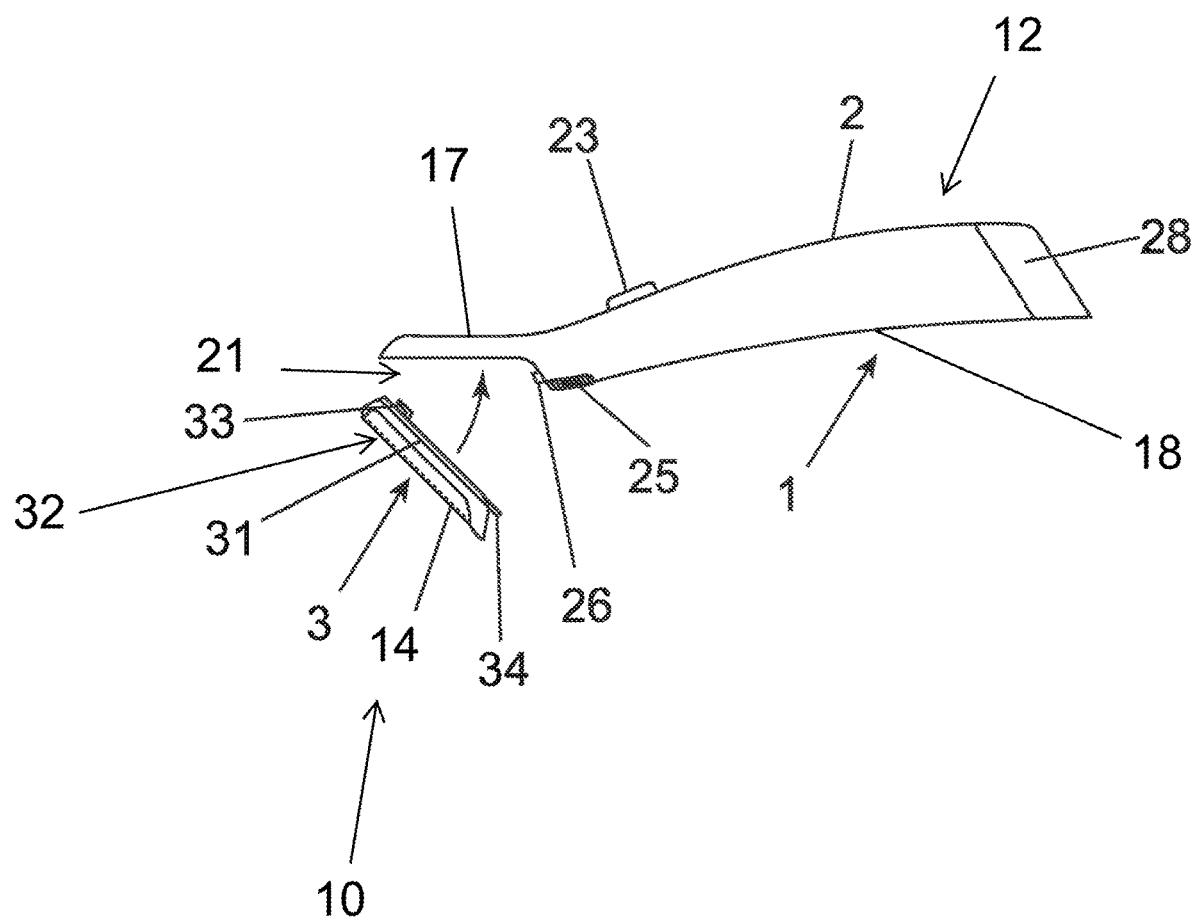
Figure 2:
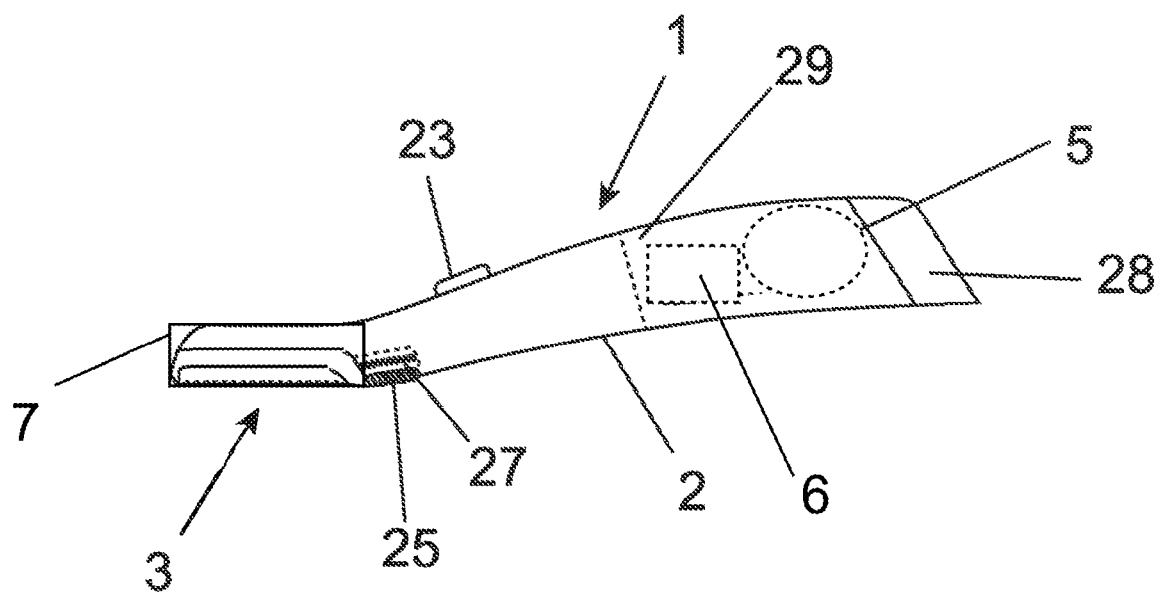
Figure 3:
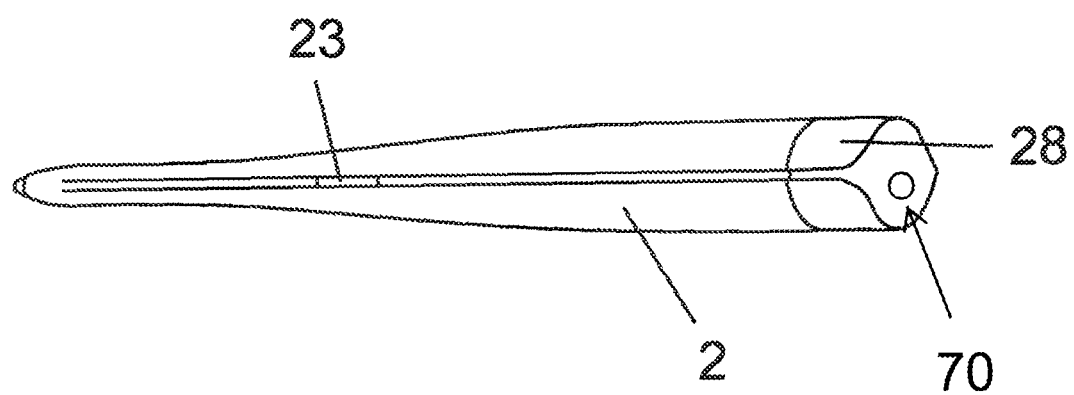
Figure 4:
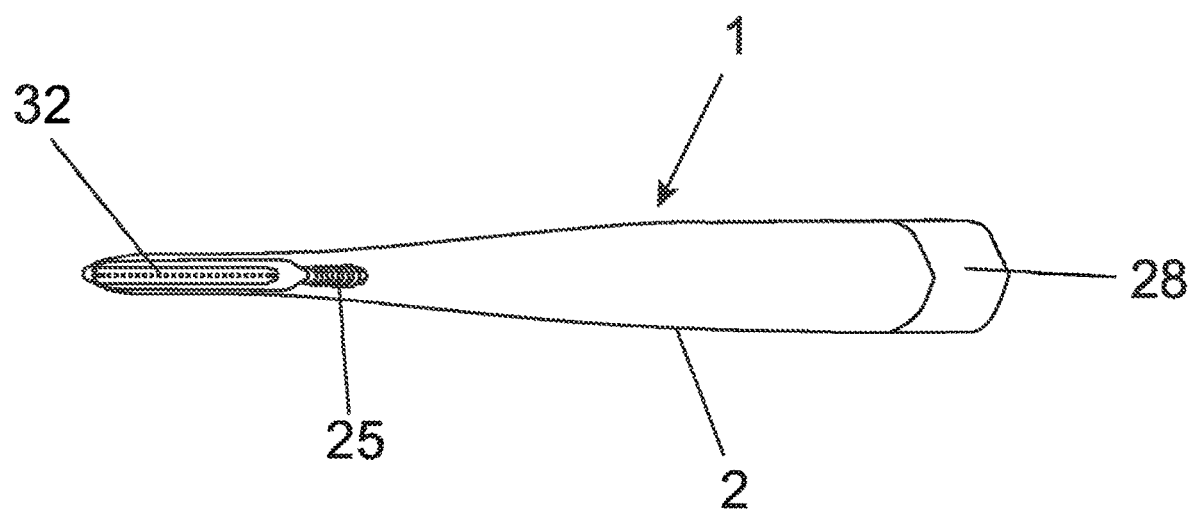
Figure 5:
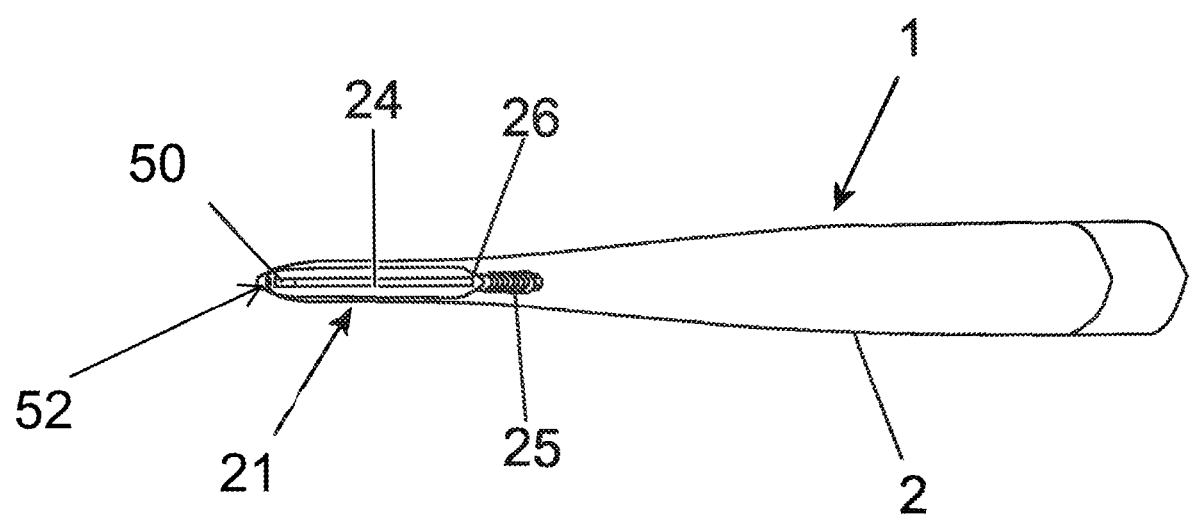
Figure 6:
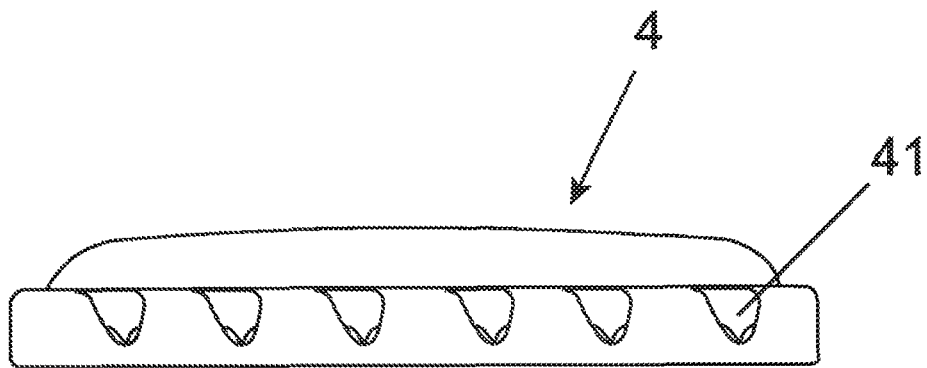
Figure 7:
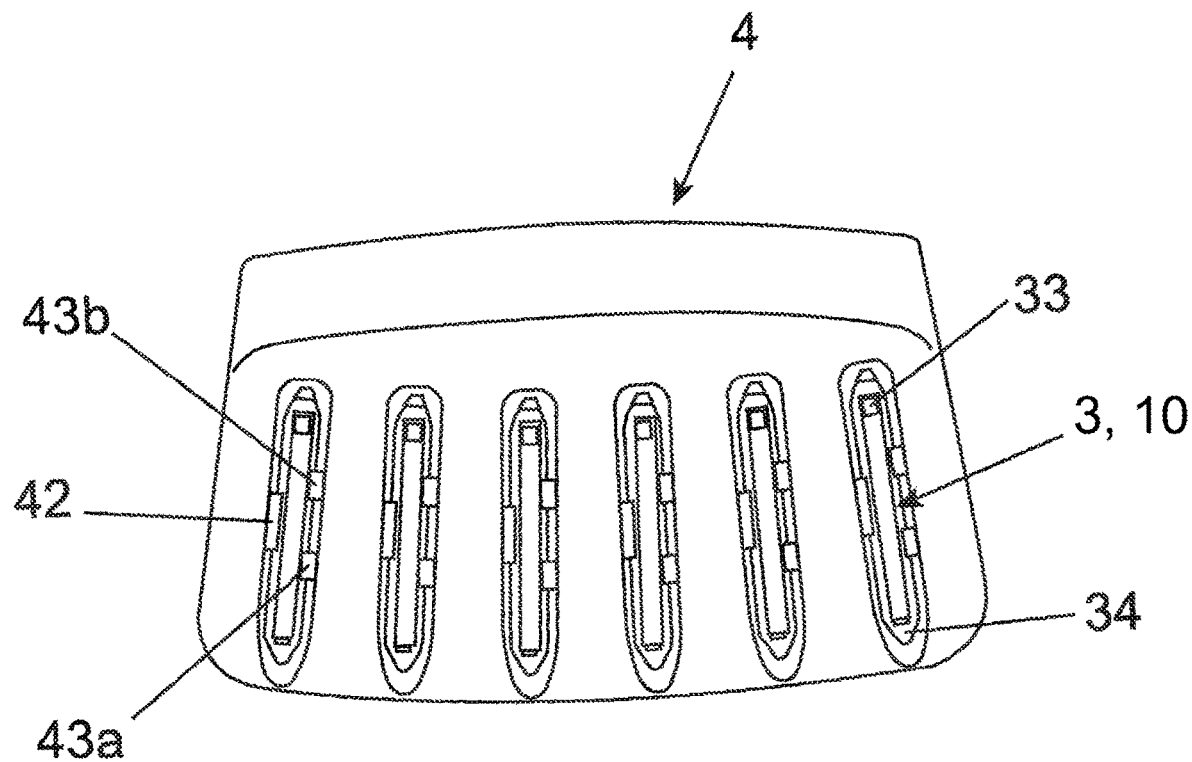
Figure 8:
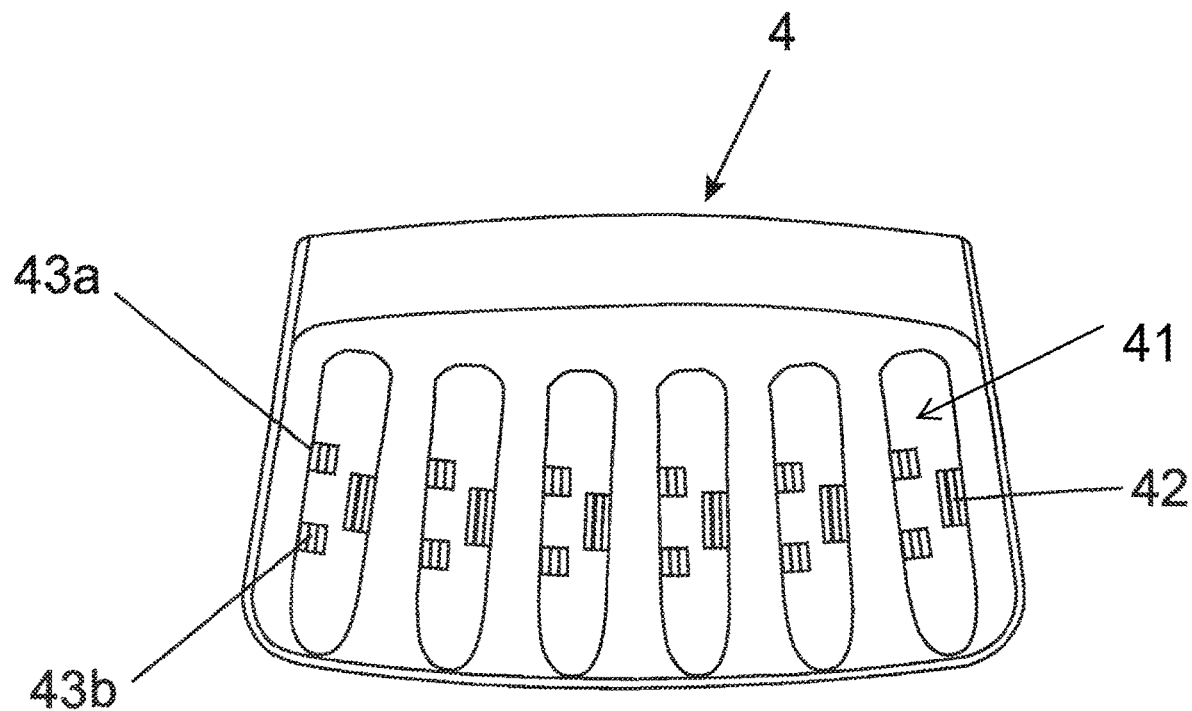
Figure 9:
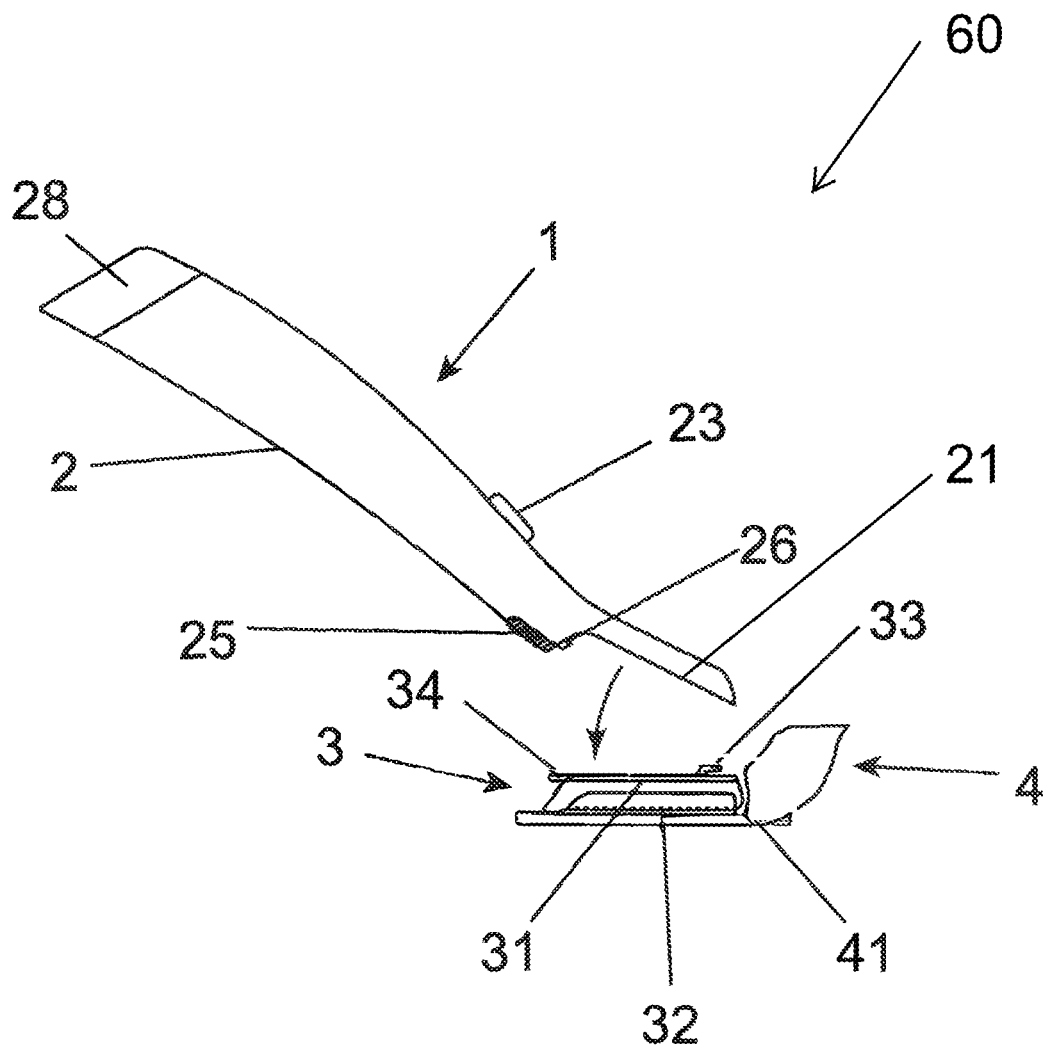
Figure 10:
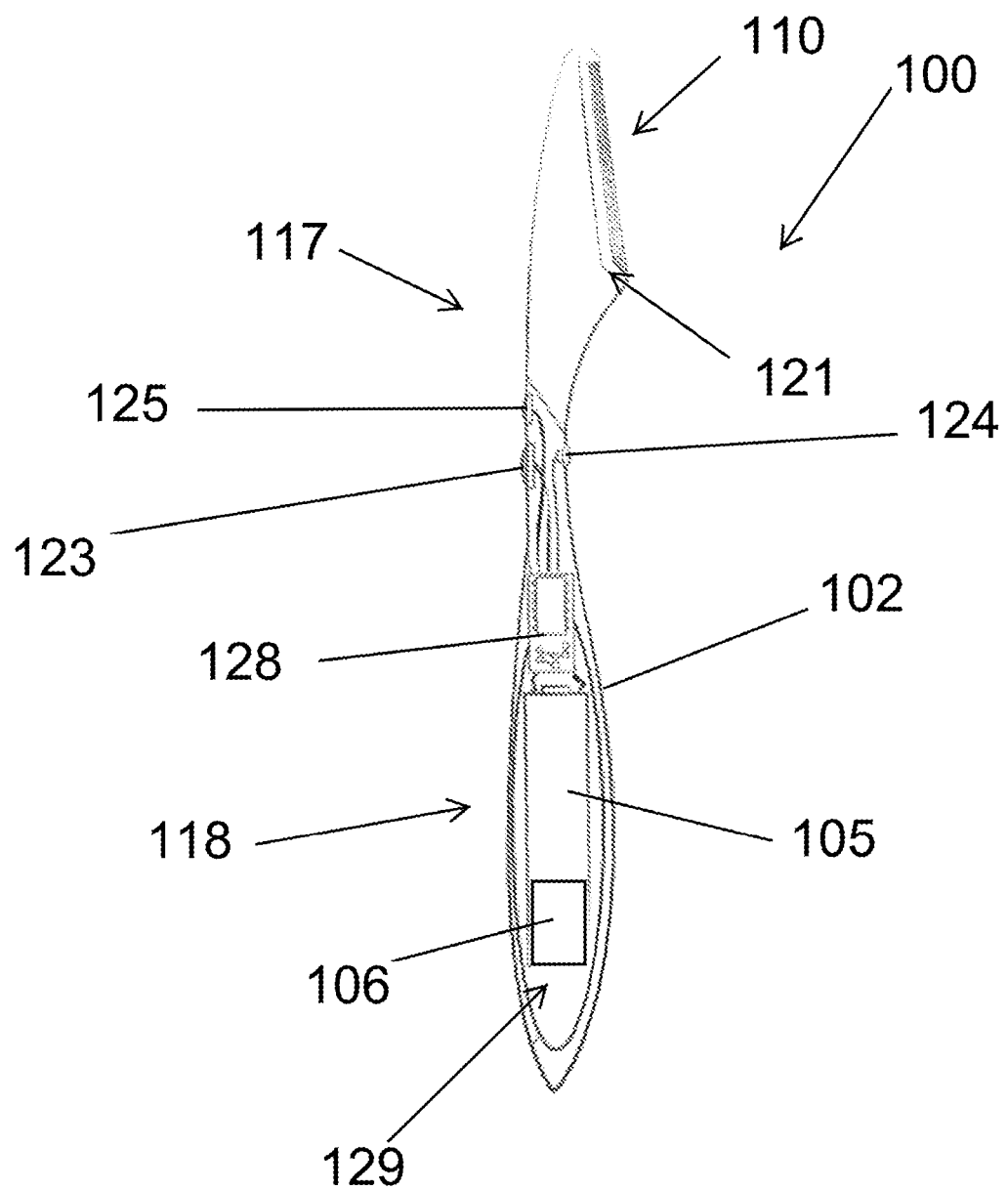
Figure 11:
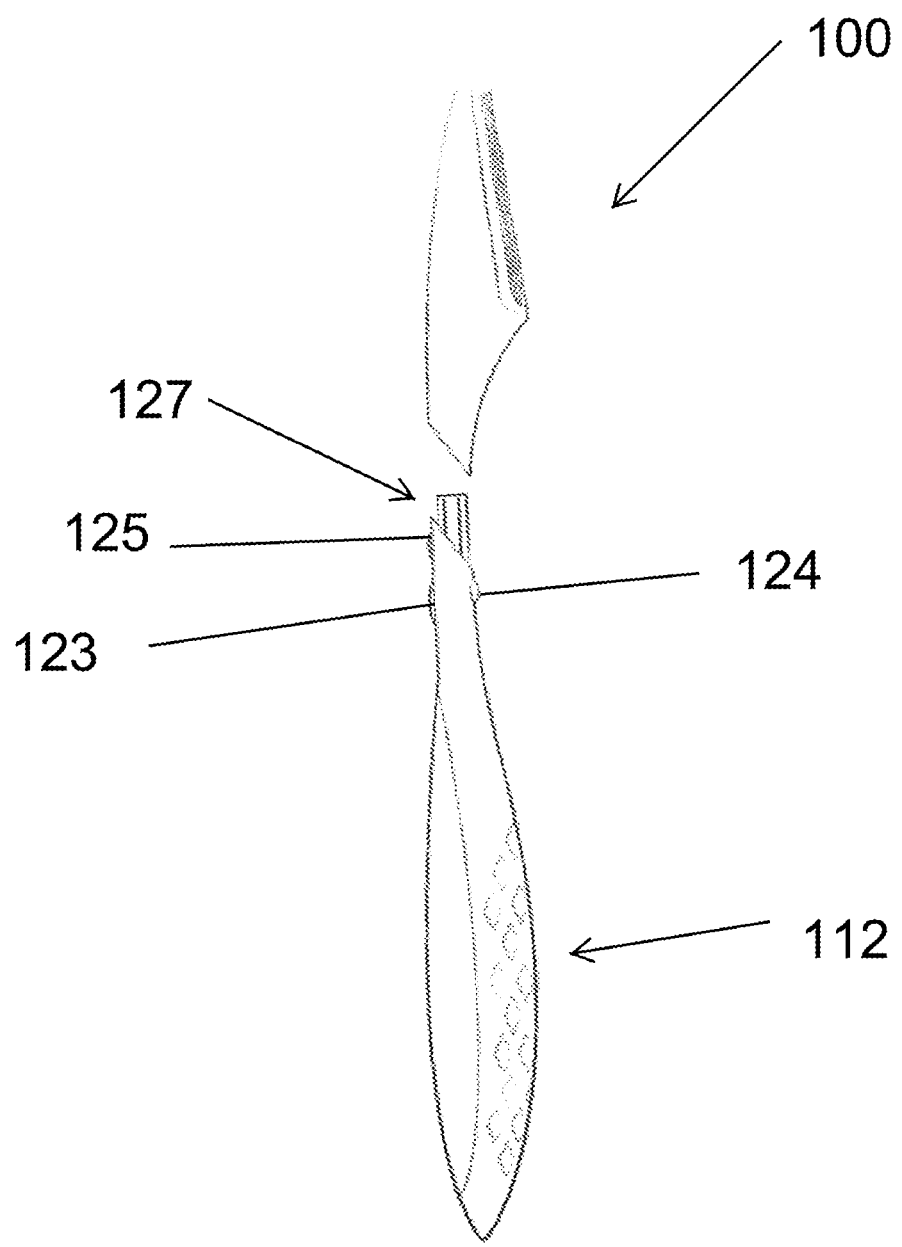
Figure 12:
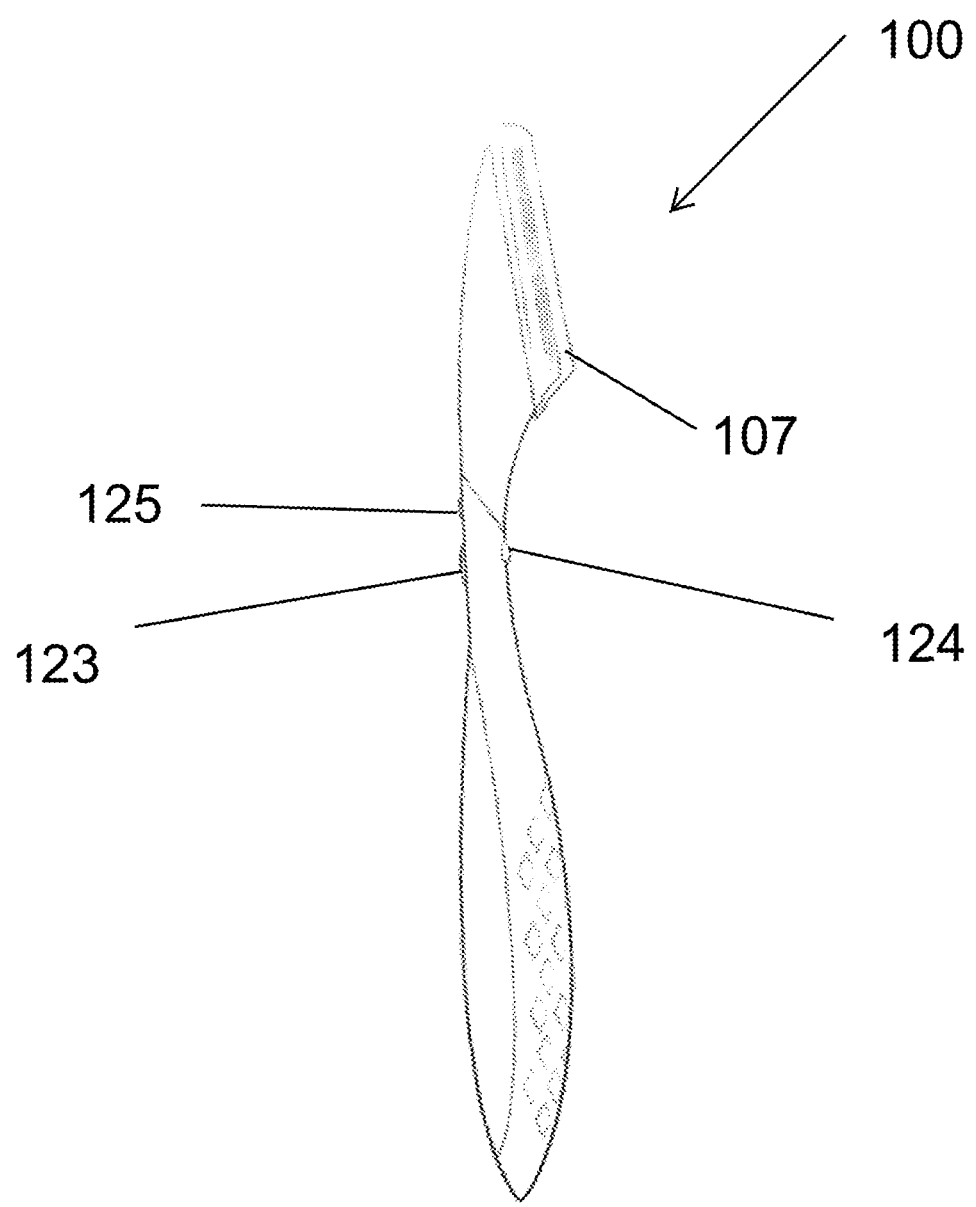
Figure 13:
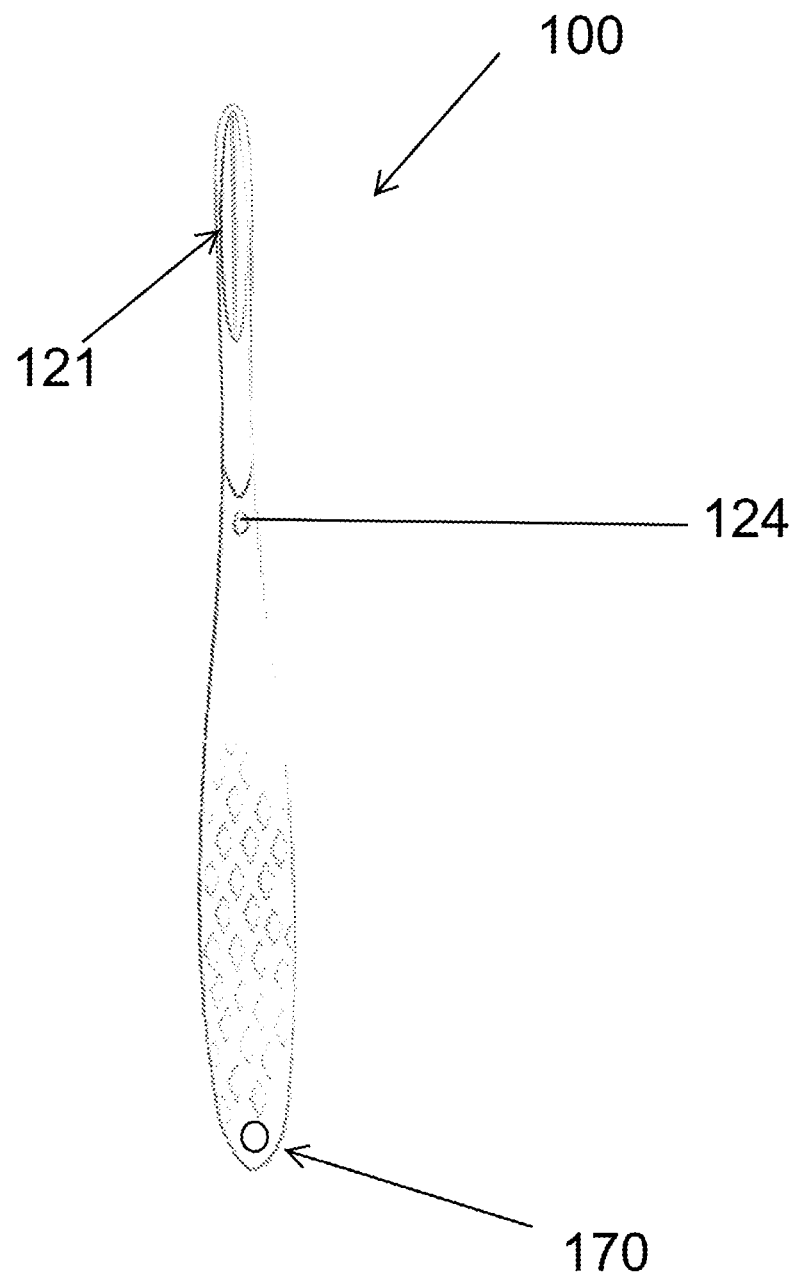
Figure 14:
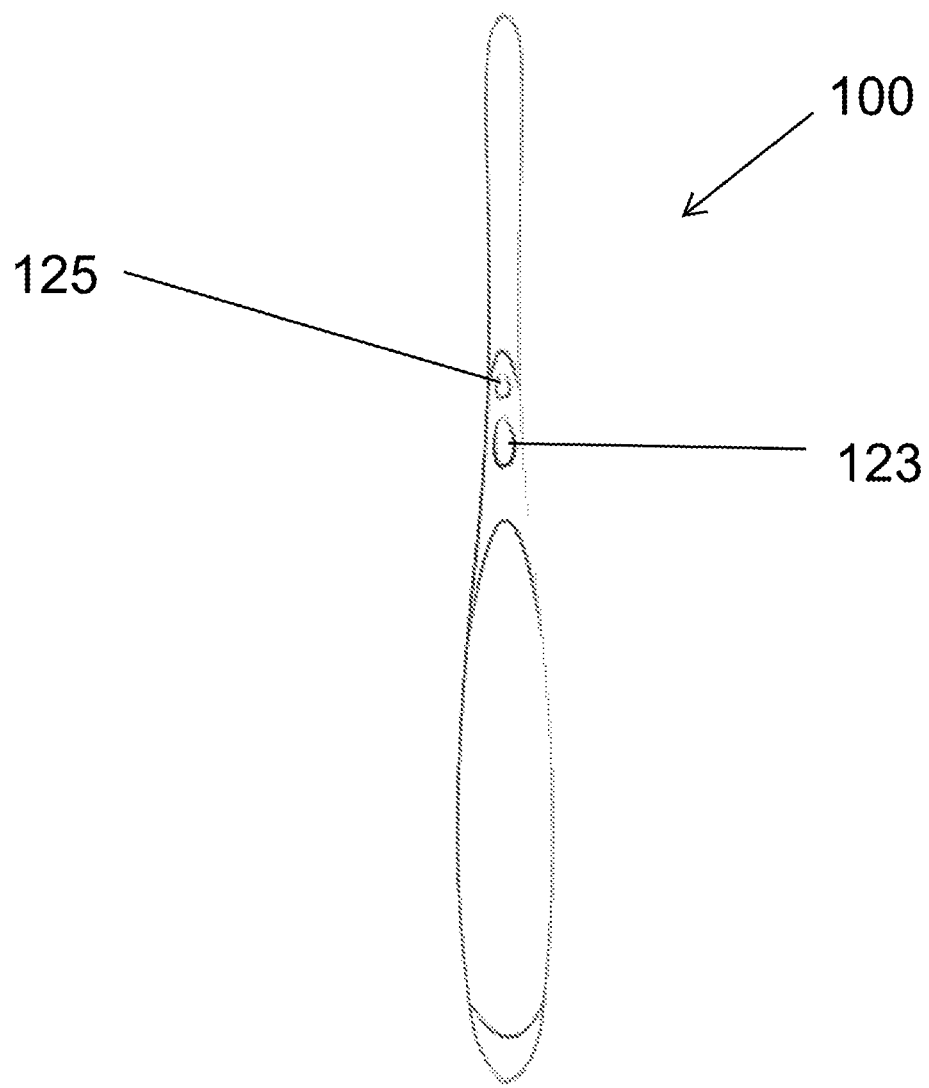
Figure 15:
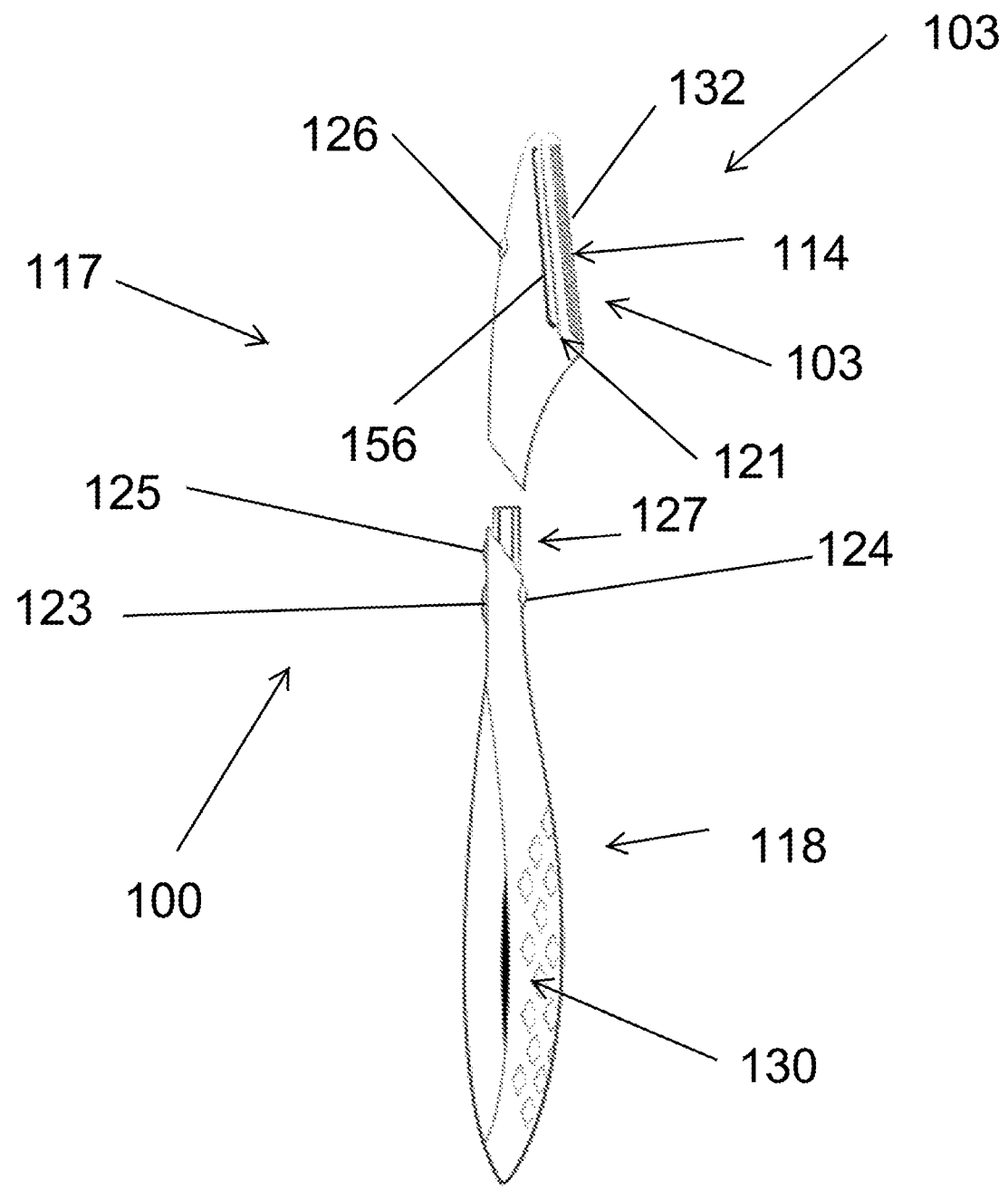
Figure 16:
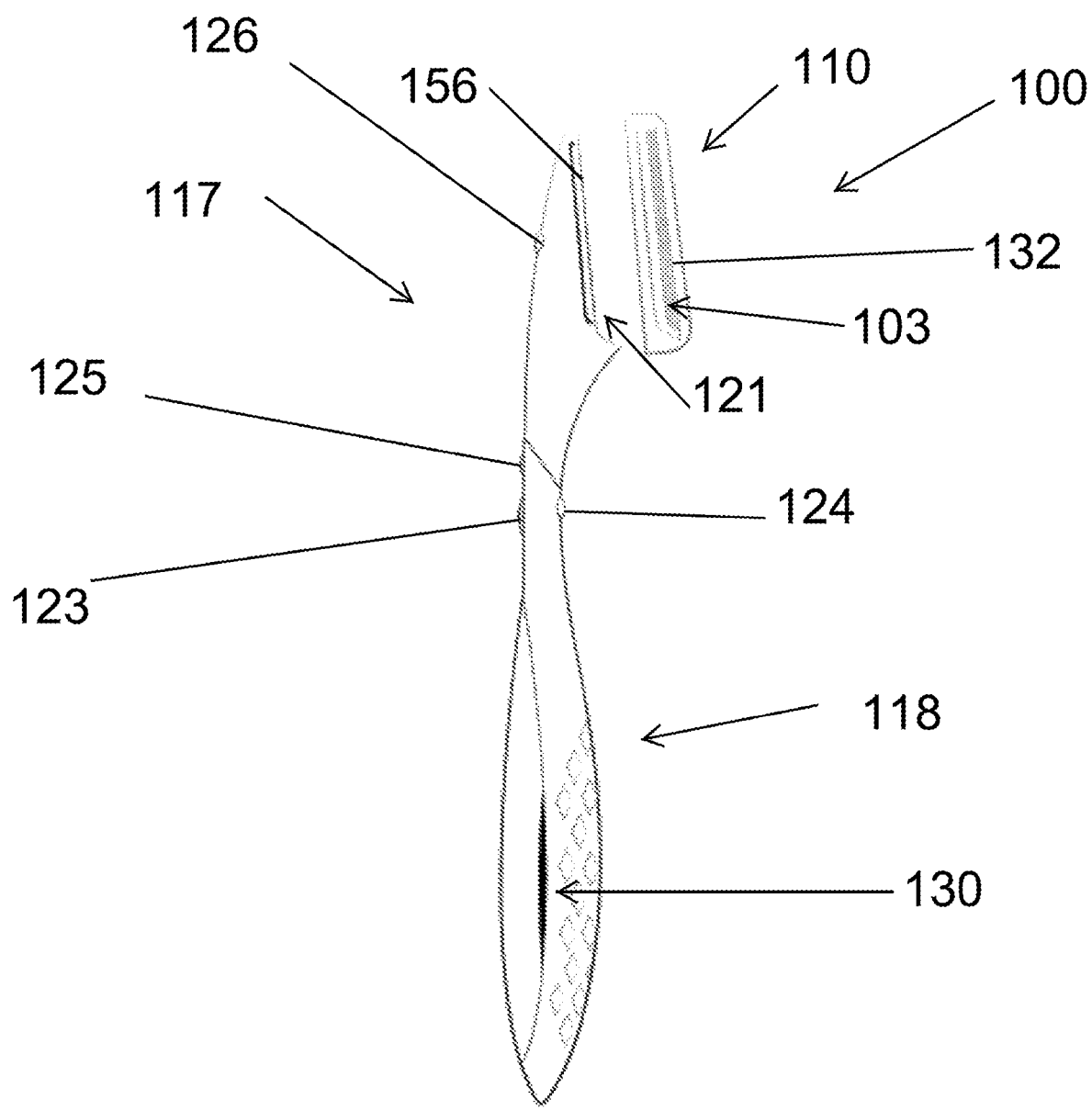
Figure 17:
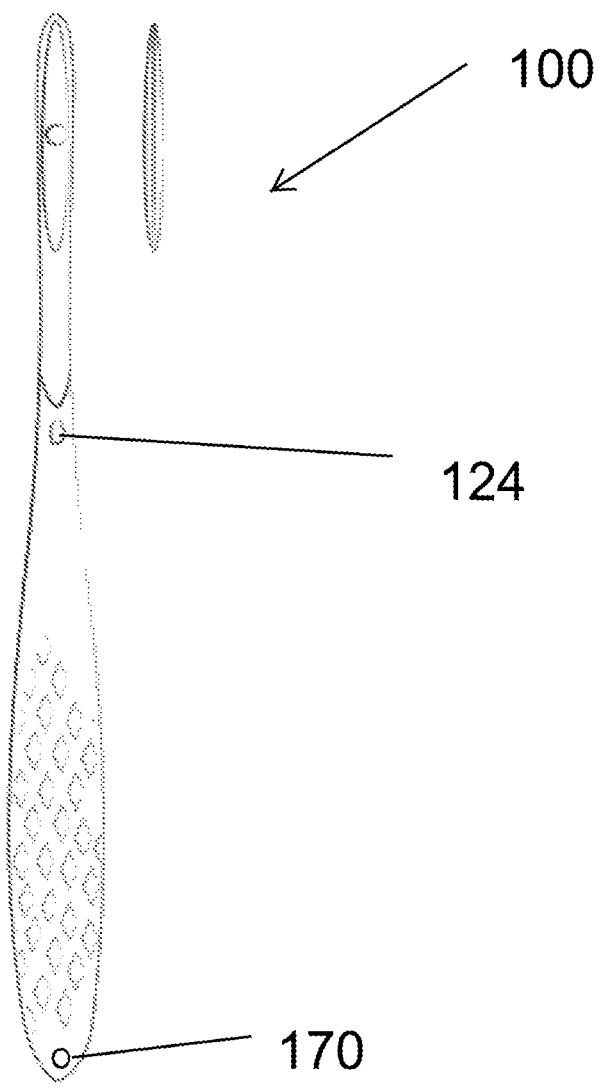
Figure 18:
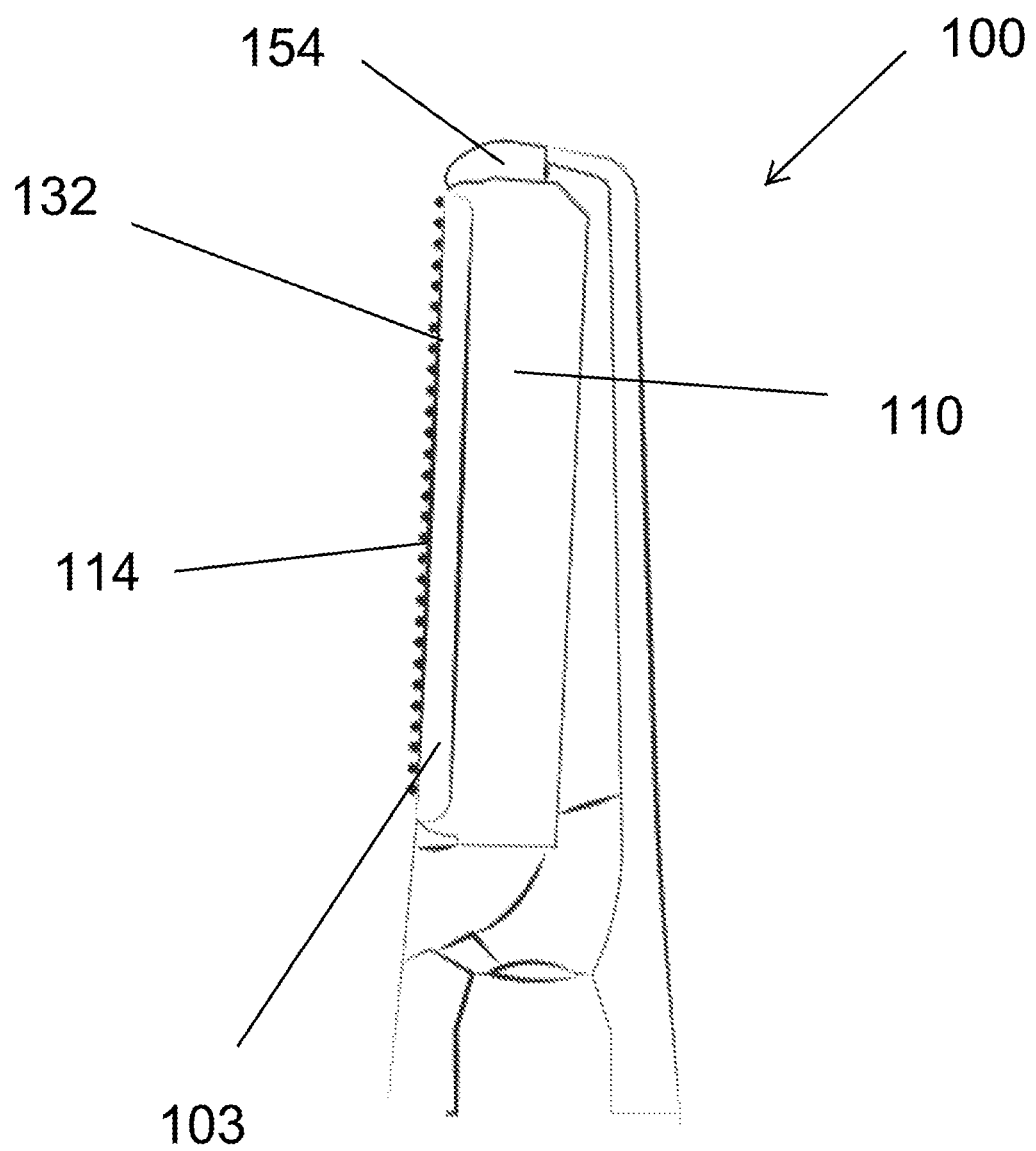
Figure 19:
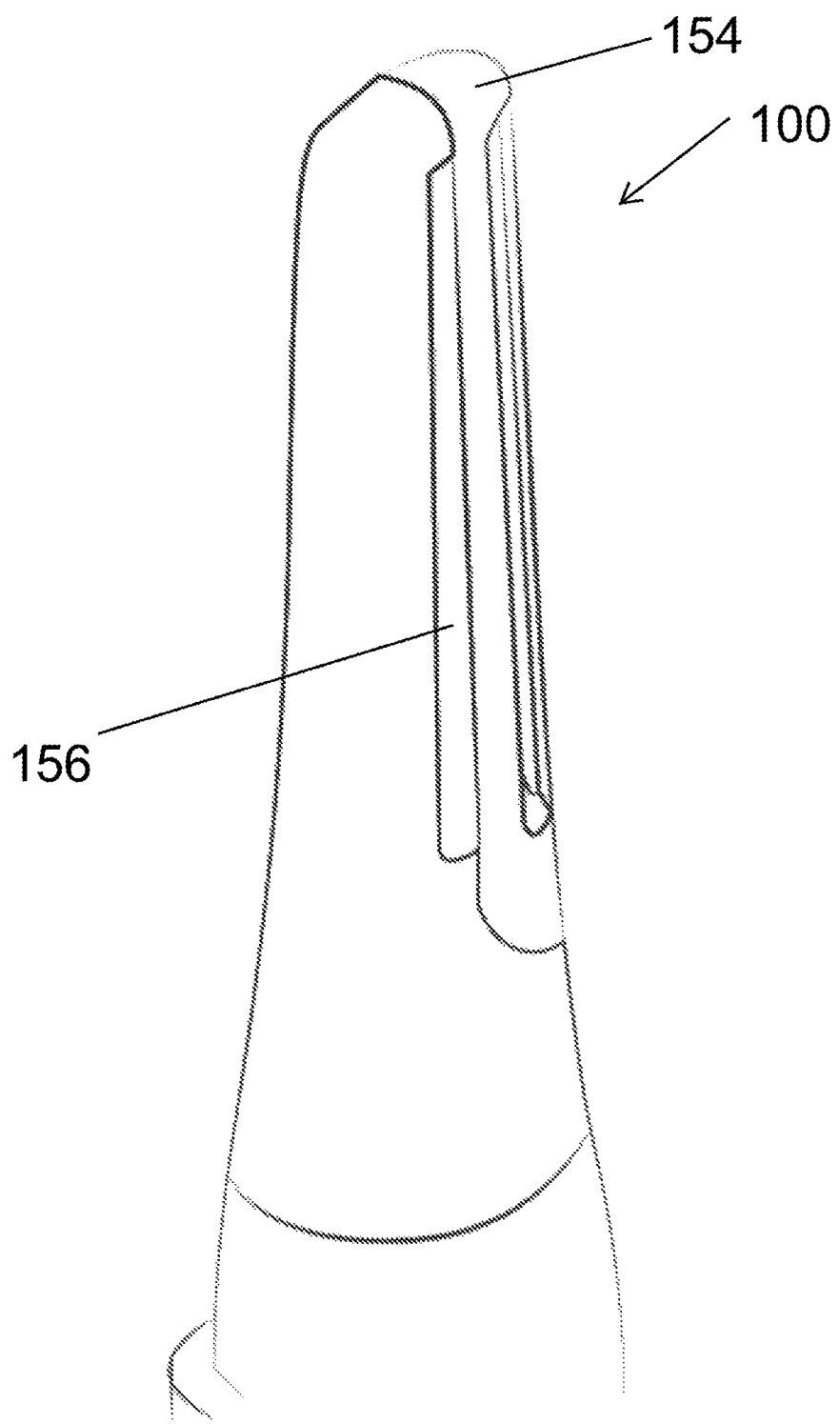
Figure 20:
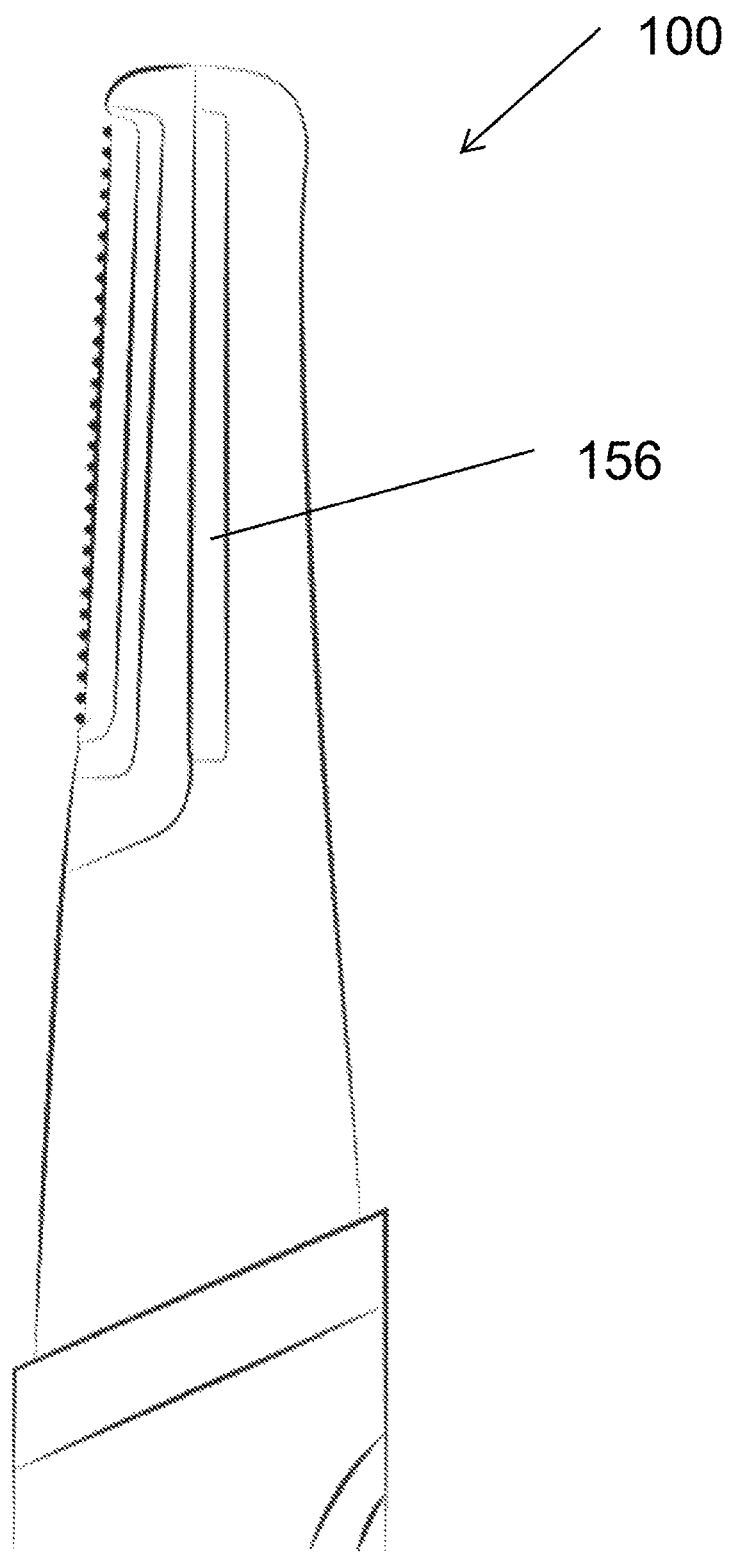
Figure 21:
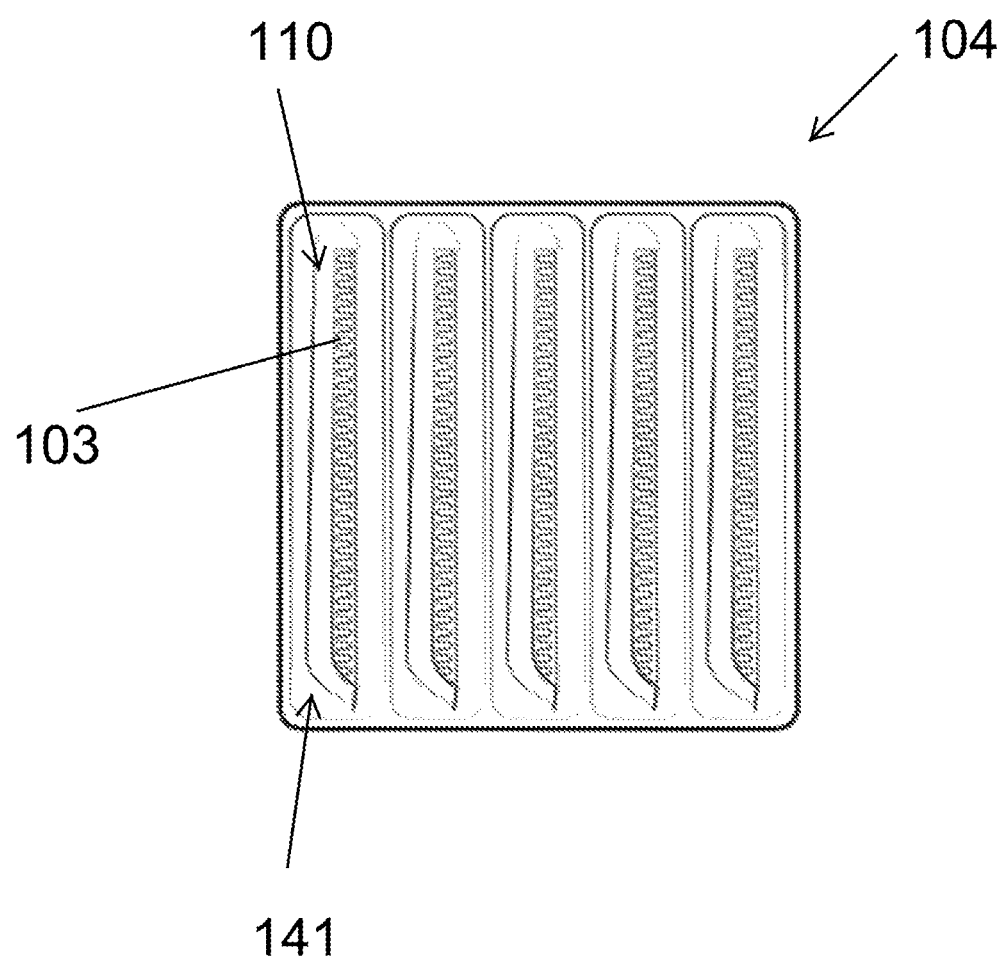
Figure 22:
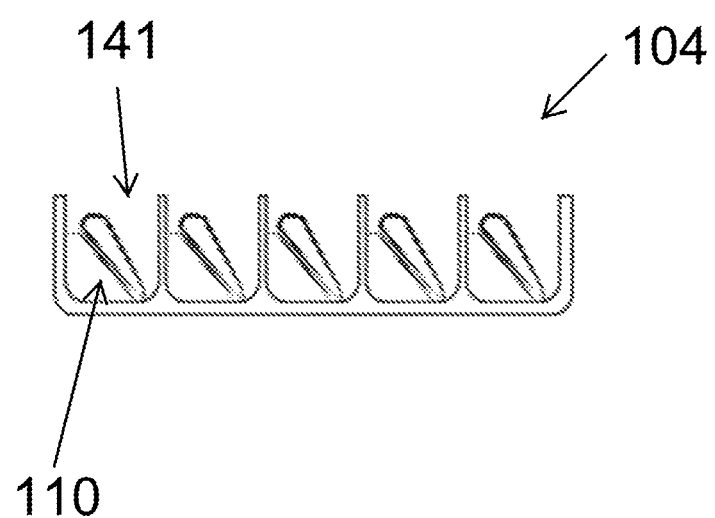

Having thus described the disclosure in general terms, reference will now be made to the accompanying drawings, which are not necessarily drawn to scale, and wherein:

FIG. 1 is a side view of a dermaplaning device according to a first example embodiment of the present disclosure with a blade assembly removed from a handle;

FIG. 2 is a side view of the dermaplaning device of FIG. 1 with the blade attached to the handle;

FIG. 3 is a top view of the dermaplaning device of FIG. 1;

FIG. 4 is a bottom view of the dermaplaning device of FIG. 1 with the blade assembly attached to the handle;

FIG. 5 is a bottom view of the dermaplaning device of FIG. 1 without the blade assembly attached to the handle;

FIG. 6 is a front view of a blade dispenser according to the first example embodiment of the present disclosure without any blade assemblies arranged in respective cavities;

FIG. 7 is a top view of the blade dispenser of FIG. 6 with blade assemblies arranged in the respective cavities;

FIG. 8 is a bottom view of the blade dispenser of FIG. 6;

FIG. 9 is a side view of a dermaplaning system according to the first example embodiment of the present disclosure and including a dermaplaning device and a blade holder;

FIG. 10 is a cross-sectional view of a dermaplaning device according to a second embodiment of the present disclosure;

FIG. 11 is a side view of the dermaplaning device of FIG. 10 with a first end of a handle including a blade assembly removed from a remainder of the handle;

FIG. 12 is a side view of the dermaplaning device of FIG. 10 with a cover over at least a portion of a blade assembly;

FIG. 13 is a front view of the dermaplaning device of FIG. 10;

FIG. 14 is a rear view of the dermaplaning device of FIG. 10;

FIG. 15 is a side view of the dermaplaning device of FIG. 10 with a first end of a handle including a blade assembly removed from a remainder of the handle and a lighting arrangement about a second end of the handle illuminated;

FIG. 16 is a side view of the dermaplaning device of FIG. 10 with a blade assembly including a blade removed from a first end of the handle and a lighting arrangement about a second end of the handle illuminated;

FIG. 17 is a front view of the dermaplaning device of FIG. 10 with a blade removed from a blade assembly;

FIG. 18 is a detailed side view of a blade assembly of the dermaplaning device of FIG. 10;

FIG. 19 is a detailed rear view of a blade assembly of the dermaplaning device of FIG. 10;

FIG. 20 is another detailed side view of a blade assembly of the dermaplaning device of FIG. 10;

FIG. 21 is a top view of a blade dispenser according to the second example embodiment of the present disclosure; and FIG. 22 is a cross-sectional view of the blade dispenser of FIG. 21.

DETAILED DESCRIPTION OF PREFERRED EMBODIMENTS

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural variations unless the context clearly dictates otherwise.

A dermaplaning device and related system as disclosed herein may be used to "dermaplane" or scrape an exterior surface of an object to remove any debris, fibers, hairs, etc., in order to leave the exterior surface smooth. In some example embodiments, the object is a mammalian user and the exterior surface is the exposed skin and, more particularly, the epidermis of the mammalian user, such that the dermaplaning device and related system may be used to scrape or skim the epidermis of the user to create a variety of cosmetic benefits for the skin. For example, using the dermaplaning device and related system disclosed herein on the epidermis of a mammalian user advantageously smooths at least the epidermis layer of the skin, exfoliates the epidermis, reduces the appearance of wrinkles and scars in the skin, promotes the production of collagen and elastin in the skin, and cleans the epidermis. The inclusion of a lighting arrangement in the dermaplaning device and system disclosed herein illuminates a select area of the epidermis to allow for more precise dermaplaning during use.

Turning now to FIGS. 1-9, a first example embodiment of a dermaplaning device and related system are disclosed. FIG. 1 illustrates a dermaplaning device 1 comprising a longitudinally-extending handle 2 having a first end 17 defining a longitudinally-extending recess 21 and an opposing second end 18. The handle may comprise plastic materials, metallic materials, wood, stone or other natural materials, recycled materials (either partially or completely), waste materials such as husks or shells from nuts, natural or man-made fibers, or any combination thereof. The recess 21 may extend longitudinally relative to a longitudinal axis of the handle 2 and be shaped and sized so as to removably or permanently engage a blade assembly 10. In some example embodiments, the first end 17 of the handle 2 defining the recess 21 is longitudinally offset from an opposing second end 18 of the handle 2. As used herein, "longitudinally offset" refers to the handle 2 having an angle relative to a horizontal surface of the recess 21. This advantageously allows a user to grip the second end 18 of the handle 2 without having the user's grip brush against the exterior surface of the object on which the dermaplaning device 1 is being used. In some example embodiments, the second end 18 of the handle may comprise a gripping region 12 allowing for a user to grip the dermaplaning device 1 during use. The gripping region 12 may be defined on the second end 18 of the handle and may comprise a similar material or a different material than the material of the handle 2. For example, the gripping region 12 may comprise elastomeric materials, metallic materials, or any combination thereof, and may have a textured surface or comprise additional materials having a lower durometer or higher coefficient of friction than the rest of the handle so as to reduce slippage.

The blade assembly 10 may be a structure having a top side defining a shelf 31 that is engageable with the recess 21 of the handle 2, and an opposing bottom side comprising a blade 3 with a cutting edge 32. A safety guard 14 may be arranged over the cutting edge 32 of the blade 3 so as to limit a cutting depth of the blade 3. The safety guard 14 may be snapped into place over the cutting edge 32 of the blade 3, or otherwise coupled to the blade so that the safety guard 14 covers at least a portion of the cutting edge 32 of the blade 3. In some example embodiments, the safety guard 14 is a comb-like structure with spaced-apart ridges extending along a length of the safety guard. In this manner, the safety guard 14 allows the cutting edge 32 to come into contact with the exterior surface of the object between the spaced-apart ridges of the safety guard 14.

The blade 3 may be any type of straight edge blade or surgical blade sharpened on one edge (i.e., the cutting edge 32). The blade 3 may comprise stainless steel, high carbon steel, or another similar material. The blade 3 may be securely arranged or sandwiched between longitudinally-extending sides of the blade assembly 10, such that the blade 3 and the blade assembly 10 are considered integral components. Otherwise, the blade 3 may be removable from the blade assembly 10 and replaceable with another blade 3.

The blade assembly 10 and the handle 2 may be engageable through one or more mechanisms, such as magnets, a press fit, a snap fit, a twist lock, a biased lock, or combinations thereof. In some example embodiments, an engagement mechanism 25, 26 may be disposed on the handle 2 of the dermaplaning device 1, wherein actuation of the engagement mechanism 25, 26 may release the blade assembly 10 including the blade 3 from engagement with the recess 21 of the handle 2. In some example embodiments, a release button 25 having a catch 26 coupled thereto may be provided adjacent to the recess 21 near the first end 17 of the handle 2. The release button 25 may be slideable in a parallel direction relative to the recess 21 and/or the handle 2 from an initial position in which the blade assembly 10 is securely engageable with the recess 21 to a second position that allows the blade assembly 10 to be released from the recess 21. In some other example embodiments, the release button 25 is slidable in a perpendicular direction relative to the recess 21 and/or the handle 2. A biasing mechanism or spring 27 (FIG. 2) may be utilized to urge the engagement mechanism 25, 26 into the initial position, such that sliding the engagement mechanism 25, 26 into the second position puts tension on the engagement mechanism 25, 26 so as to urge the engagement mechanism 25, 26 back into the initial position once sliding pressure is removed. The engagement mechanism 25, 26 may also be any other type of mechanism that is arranged to engage and release the blade assembly 10.

In particular embodiments, the catch 26 of the engagement mechanism may be configured to engage a portion of the blade assembly 10. For example, the catch 26 of the handle 2 may extend into the recess 21 in the initial position of the engagement mechanism 25, 26 so as to engage with a step 34 (FIG. 1) of the blade assembly 10. The step 34 may be arranged so that it extends from a first end 17 of the shelf 31 of the blade assembly 10, where the shelf 31 is raised and longitudinally extends along the top side of the blade assembly 10 and is sized and shaped to be received within the recess 21. Thus, when the engagement mechanism 25, 26 is in the initial position, the step 34 may slide above the catch 26 so that the step 34 rests between the catch 26 and a surface of the recess 21. When the engagement mechanism 25, 26 is slid into the second position, the catch 26 may likewise slide away from the recess 21 so that the step 34 no longer rests on the catch 26.

Further, for more secure engagement of the blade assembly 10 with the recess 21, the blade assembly 10 may engage with a portion of the recess 21 via a protrusion 33 (FIG. 1). In particular, and in some example embodiments, the protrusion 33 (FIG. 1) may be arranged to extend from a second opposing end of the shelf 31 of the blade assembly 10. The protrusion 33 may comprise a hooked end that engages a portion 50 (FIG. 5) of the recess 21 and slides into a notched area 52 (FIG. 5) of the first end 17 of the handle 2. As illustrated in FIG. 5, the portion 50 may be separated from a remaining portion of the recess 21 by a dividing line or barrier, so as to separately receive the protrusion 33 of the blade assembly 10. In this manner, the blade assembly 10 is attachable to and removable from the first end 17 of the handle 2.

In some example implementations, a lighting arrangement 24 (FIG. 5) may be provided about the first end 17 of the handle 2 to illuminate at least a portion of the blade assembly 10 engaged with the recess 21. For example, and as illustrated in FIG. 5, the lighting arrangement 24 may be arranged on the first end 17 of the handle 2 and adjacent to the recess 21; and more particularly, may extend along a length of the recess 21. In other embodiments, the lighting arrangement 24 is arranged within the blade assembly 10 or the handle 2.

The lighting arrangement 24 may include a light source, such as one or more light-emitting diode (LED), an incandescent light, a halogen light, an electroluminescent light, a fluorescent light, a bioluminescent light, a laser light, a chemiluminescent light, a phosphorescent light, a photoluminescent light, or combinations thereof. The type of light source utilized in the lighting arrangement 24 may result in differently colored illumination. For example, the light source may have a color spectrum that emits yellow light, white light, blue light, red light, etc. In this manner, it may be desirable to use two or more light sources having different spectra in the lighting arrangement 24, where the different light sources may or may not overlap in their spectra.

Further, the different light sources in the lighting arrangement 24 may be controlled to flash, blink, remain constantly on, etc., to indicate different states of the device 1 and/or regions of the exterior surface of the object. For example, a red light may flash when a power source 5 needs recharging, a green light may flash when the device 1 is fully charged, one of the light sources may turn off or change color once the blade 3 is in contact with the exterior surface, etc. The lighting arrangement 24 may also include a light guide or light pipe positioned adjacent to the blade assembly 10, so as to direct and control a pattern of illumination emanating from the dermaplaning device 1. More particularly, the light guide may extend along the recess 21 so as to form an illumination area emanating from the recess 21. The illumination area may be a line projected onto the exterior surface of the object or a circular region projected onto the exterior surface of the object. The illumination area on the exterior surface of the object may indicate where the cutting edge 32 of the blade 3 will contact the exterior surface so as to make the dermaplaning experience easier for the user. The light guide may also illuminate at least a side of the blade 3, a region surrounding the blade 3, or any combination thereof.

As illustrated in FIG. 2, a power source 5 may be in electric communication with the light source of the lighting arrangement 24. The power source 5 may be one of a rechargeable battery, a disposable battery, or any other type of power storage mechanism. In some example embodiments, and as illustrated in FIG. 2, the power source 5 may be arranged about the second end 18 of the handle 2, although other arrangements of the power source 5 are also contemplated. For example, the second end 18 of the handle 2 may define an internal compartment or cavity 29, as illustrated in FIG. 2, that is arranged to contain the power source 5 therein. A rear cover 28 may be removably attached to the second end 18 of the handle 2 so as to cover the internal compartment or cavity 29. As such, the power source 5 may be removable from the internal compartment 29 through removal of the rear cover 28, or the power source 5 may remain within the internal compartment 29 and may be rechargeable. A seal, gasket, or other device to prevent moisture and humidity from entering the internal compartment 29 may be provided about the second end 18 of the handle 2, as well.

In order to facilitate usage of the lighting arrangement 24 of the dermaplaning device 1, in some example embodiments, the blade assembly 10 (i.e., the structure) may comprise a translucent material such that light from the light source of the lighting arrangement 24 may pass through the translucent material of the blade assembly 10 so as to illuminate at least a portion of the blade assembly 10 and thereby a target area during use of the dermaplaning device 1. Alternatively, the blade assembly 10 may comprise a transparent material, or any other type of material that allows light to pass through the blade assembly 10. However, the dermaplaning device 1 is still usable without the lighting arrangement 24 and the blade 3 may still be utilized to scrape against the exterior surface of the object without the lighting arrangement 24 providing illumination. It is advantageous to use the lighting arrangement 24, though, in order to illuminate a region on the exterior surface of the object to be dermaplaned and thus allow for more precise usage of the dermaplaning device 1.

In some example embodiments, the dermaplaning device 1 may comprise a charging system (not shown) for charging the power source 5, where the power source 5 is a rechargeable power storage device (e.g., rechargeable battery). The charging system may receive energy through motion, an electrical connection, light, induction, a magnetic field, radiofrequency, or other wireless means. For example, the charging system may include a cable that is insertable through a port 70 (FIG. 3) defined in the device 1 and electrically connected to the power source 5 and an external power source, such as a wall socket.

A switch or power button 23 may be provided on the handle 2. The switch 23 may be depressible or otherwise actuatable. The switch 23 may be in electric communication with the power source 5, and may be arranged to activate the power source 5 and thereby illuminate at least a portion of the blade assembly 10 when actuated. More particularly, the switch 23, the power source 5, and the lighting arrangement 24 may be connected together with a circuit board (e.g., a printed circuit board), such that when the switch 23 is activated the formed circuit is completed and electricity is flowable from the power source 5 to the lighting arrangement 24.

In some example embodiments, a motor 6 may be in electric communication with the power source 5 and the blade 3, wherein the motor 6 is configured to cause one or both of vibration and reciprocation of the blade 3 upon actuation of the motor 6. More particularly, the switch 23, the power source 5, the blade 3, the motor 6 and/or the lighting arrangement 24 may form a circuit, such that when the switch 23 is activated the circuit is completed and electricity is flowable from the power source 5 to the motor 6 so as to cause the blade 3 to move, and/or the lighting arrangement 24 to illuminate the region on the exterior surface of the object. The motor 6 may have different settings, so that different vibrational or reciprocating speeds and patterns may cause the blade 3 to move differently in response thereto. The different settings may be desirable where, for example, different types of hair or skin are being scraped with the blade 3 and require different amounts of scraping force.

In some example embodiments, a sensor mechanism (not shown) may be incorporated with the circuit. The sensor mechanism may be a type of mechanism that is able to determine if the user is using the device 1 correctly, e.g., is applying enough pressure, user is holding the device at the desired angle, etc. The sensor mechanism may be a capacitive sensor, an accelerometer, pressure sensors, electrical conductivity sensors, optical sensors, force sensors, or combinations thereof. Feedback may be reported to the user via different colored lights, vibrations, and the like. For example, the sensor mechanism may be configured to detect whether the dermaplaning device 1 is being held, and as a result, output a signal to the lighting arrangement 24 to automatically provide illumination.

In some example embodiments, an icon (not shown) may be illuminated based on a state of the dermaplaning device 1 and/or certain actions of the user. For example, the icon may be in electrical communication with the sensor mechanism and become illuminated in response to an output from the sensor mechanism. In this example, the sensor mechanism may be a pressure sensor that measures the contact pressure between the exterior surface of the object and the device 1 and outputs a signal to the lighting arrangement 24 to illuminate the icon if the contact pressure applied corresponds to a pre-determined amount. In another example, the sensor mechanism may be a gyroscope that measures the angle at which the user is holding the device 1 and outputs a signal to the lighting arrangement 24 to illuminate the icon if the angle corresponds to a pre-determined angle of use. In some example embodiments, the light output may be different colors in either example depending on the signal. A red light may illuminate the icon if the angle or contact pressure does not correspond to the pre-determined amount, and a green light may illuminate the icon if the angle or contact pressure corresponds to the pre-determined amount.

Referring to FIG. 2, a cover 7 may be arrangeable about the first end 17 of the handle 2 so as to enclose at least the cutting edge 32 of the blade 3. The cover may be a translucent material, a transparent material, or any combination thereof so that a user can see through the cover to ascertain whether a blade 3 is attached to the blade assembly 10. As illustrated in FIG. 2, for example, the cover extends over the first end 17 of the handle 2 so as to cover the first end 17 of the handle 2 as well as the blade assembly 10 and the blade 3. The cover 7 may remain in place on the dermaplaning device 1 through depressions formed on the cover that align with and are retained by small protrusions formed on the second end 18 of the blade assembly 10. The depressions on the cover 7 may be pressed against the protrusions of the blade assembly 10 when the cover is engaged with the blade assembly 10, so that the cover 7 is not removable unless pressure is applied thereto. In some example embodiments, the blade assembly 10 may not be removable from the handle 2 without the cover 7 enclosing at least the cutting edge 32 of the blade 3.

Referring now to FIGS. 6-8, a blade dispenser 4 is illustrated. The blade dispenser 4 may be a component or element of a dermaplaning system 60 (FIG. 9) that includes a dermaplaning device, such as the dermaplaning device 1. The blade dispenser 4 may define a plurality of cavities 41, each cavity 41 being arranged to retain a blade assembly 10 including a blade 3 therein and dispense the blade assembly 10 upon engagement of the top side of the blade assembly 10 with the recess 21 of the dermaplaning device 1. In this manner, a user may change blade assemblies 10 without having to directly contact the blade assemblies 10, and thereby the blade 3. In some example embodiments, the cavities 41 are arranged to fan out, although in other example embodiments the cavities 41 are arranged parallel to one another, are in staggered formation relative to one another, etc. As illustrated in FIGS. 7 and 8, the cavities are arranged fanning out from one another and a blade 3 is received in each of the cavities 41. A first gripping element 42 and second gripping elements 43a, 43b are provided in each of the cavities 41 to retain each blade 3 within its respective cavity. When a blade assembly 10 is placed within a cavity 41, the first gripping element 42 and the second gripping elements 43a, 43b are biased against the shelf 31 of the blade assembly 10 in order to retain the blade assembly 10 in place.

FIG. 9 illustrates a dermaplaning system 60 including the dermaplaning device 1 interacting with the blade dispenser 4 so as to engage a blade 3 in a blade assembly 10 with a recess 21 of the dermaplaning device 1. As shown in FIG. 9, the dermaplaning device 1 is brought into alignment with the blade assembly 10 retained in the blade dispenser 4 so that the shelf 31, the protrusion 33, and the step 34 may be engaged with the recess 21 of the dermaplaning device 1. Once engagement between these elements occurs, the dermaplaning device 1 may be lifted away from the blade dispenser 4 so that the first and second gripping elements 42, 43a, 43b release the shelf 31 of the blade assembly 10.

Referring now to FIGS. 10-22, a second example embodiment of a dermaplaning device and related system are disclosed. FIG. 10 illustrates a dermaplaning device 100 comprising a longitudinally-extending handle 102 having a first end 117 defining a longitudinally-extending recess 121 (FIG. 13) and an opposing second end 118. The handle may comprise plastic materials, metallic materials, wood, stone or other natural materials, recycled materials (either partially or completely), waste materials such as husks or shells from nuts, natural or man-made fibers, or any combination thereof. The recess 121 may extend longitudinally relative to a longitudinal axis of the handle 102 and be shaped and sized so as to removably or permanently engage a blade assembly 110. In some example embodiments, the first end 117 of the handle 102 defining the recess 121 is longitudinally offset from an opposing second end 118 of the handle 102. As used herein, "longitudinally offset" refers to the handle 102 having an angle relative to a horizontal surface of the recess 121. This advantageously allows a user to grip the second end 118 of the handle 102 without having the user's grip brush against the exterior surface of the object on which the dermaplaning device 100 is being used.

In some example embodiments, the second end 118 of the handle 102 may comprise a gripping region 112 (FIG. 11) allowing for a user to grip the dermaplaning device 100 during use. The gripping region 112 may be defined on the second end 118 of the handle 102 and may comprise a similar material or a different material than the material of the handle 102. For example, the gripping region 112 may comprise elastomeric materials, metallic materials, or any combination thereof, and may have a textured surface or comprise additional materials having a lower durometer or higher coefficient of friction than the rest of the handle so as to reduce slippage.

As illustrated in FIG. 16, the blade assembly 110 may be a structure having a top side that is engageable with the recess 121 of the handle 102, and an opposing bottom side comprising a blade 103 with a cutting edge 132. A safety guard 114 (FIG. 18) may be arranged over the cutting edge 132 of the blade 103 so as to limit a cutting depth of the blade 103. The safety guard 114 may be snapped into place over the cutting edge 132 of the blade 103, or otherwise coupled to the blade so that the safety guard 114 covers at least a portion of the cutting edge 132 of the blade 103. In some example embodiments, the safety guard 114 is a comb-like structure with spaced-apart ridges extending along a length of the safety guard. In this manner, the safety guard 114 allows the cutting edge 132 to come into contact with the exterior surface of the object between the spaced-apart ridges of the safety guard 114.

The blade 103 may be any type of straight edge blade or surgical blade sharpened on one edge (i.e., the cutting edge 132). The blade 103 may comprise stainless steel, high carbon steel, or another similar material. The blade 103 may be securely arranged or sandwiched between longitudinally-extending sides of the blade assembly 110, such that the blade 103 and the blade assembly 110 are considered integral components. Otherwise, the blade 103 may be removable from the blade assembly 110 and replaceable with another blade 103.

The blade assembly 110 and the handle 102 may be engageable through one or more mechanisms, such as magnets, a press fit, a snap fit, a twist lock, a biased lock, or combinations thereof. In some example embodiments, an engagement mechanism 125 may be disposed on the handle 102 of the dermaplaning device 100, wherein actuation of the engagement mechanism 125 may release the blade assembly 110 including the blade 103 from engagement with the recess 121 of the handle 102. For example, the engagement mechanism 125 may be a depressible, spring-loaded button coupled to an internal catch (not shown). In an initial position of the engagement mechanism 125, the internal catch may be coupled with at least a portion of the blade assembly 110 (e.g., a protrusion) so as to retain the blade assembly 110 in engagement with the recess 121 of the handle 102. The button may be biased by a spring (not shown) into the initial position. Upon depression of the button into a second position, the internal catch may move out of engagement with the blade assembly 110 so as to release the blade assembly 110 including the blade 103 from engagement with the recess 121. The spring may urge the button back into the initial position once the button is no longer depressed.

The dermaplaning device 100 also comprises, in some example embodiments, an ejection mechanism (not shown). The ejection mechanism may be a button, sliding mechanism, or the like that may be actuated to release a portion of the handle 102 including the first end 117 from a remaining portion of the handle 102. FIGS. 11 and 15 illustrates a portion of the handle 102 including the first end 117 released from a remaining portion of the handle 102. Otherwise, in some example embodiments, the portion of the handle 102 including the first end 117 may be coupled to the remaining portion of the handle 102 using magnets, a screw fit, a press fit, or the like. In some other example embodiments, the handle 102 is an integrally-formed unit.

In some example implementations, a lighting arrangement 124 may be provided about the first end 117 of the handle 102 to illuminate at least a portion of the blade assembly 110 engaged with the recess 121. For example, the lighting arrangement 124 may be arranged about the first end 117 of the handle 102 and adjacent to the recess 121. In other embodiments, the lighting arrangement 124 is arranged within the blade assembly 110 or the handle 102. For example, and as illustrated in FIGS. 15 and 16, there are two lighting arrangements: lighting arrangement 124 arranged about the first end 117 of the handle 102 and a second lighting arrangement 130 arranged about the second end 118 of the handle 102.

The lighting arrangement 124 and/or lighting arrangement 130 may include a light source, such as one or more LED, an incandescent light, a halogen light, an electroluminescent light, a fluorescent light, a bioluminescent light, a laser light, a chemiluminescent light, a phosphorescent light, a photoluminenscent light, or combinations thereof. The type of light source utilized in the lighting arrangement 124 and/or lighting arrangement 130 may result in differently colored illumination. For example, the light source may have a color spectrum that emits yellow light, white light, blue light, red light, etc. In this manner, it may be desirable to use two or more light sources having different spectra in the lighting arrangement 124 and/or lighting arrangement 130, where the different light sources may or may not overlap in their spectra. As illustrated in FIGS. 15 and 16, for example, there are two different lighting arrangements, where each lighting arrangement 124, 130 may share one light source or may each having their own light source. Where the lighting arrangements 124, 130 each having different light sources, these light sources may be different or similar types of light sources with different or similar spectra.

Further, the different light sources in the lighting arrangement 124 and/or lighting arrangement 130 may be controlled to flash, blink, remain constantly on, etc., to indicate different states of the device 100 and/or regions of the exterior surface of the object. For example, a red light may flash when a power source 105 needs recharging, a green light may flash when the device 100 is fully charged, one of the light sources may turn off or change color once the blade 103 is in contact with the exterior surface, etc. The lighting arrangement 124 and/or lighting arrangement 130 may also include a light guide or light pipe 154 (FIGS. 18 and 19) positioned adjacent to the blade assembly 110, so as to direct and control a pattern of illumination emanating from the dermaplaning device 100. More particularly, the light guide 154 may at least partially or substantially surround the blade assembly 110 so as to direct the illumination to the blade 103 and form an illumination area emanating therefrom. The illumination area may be a line projected onto the exterior surface of the object or a circular region projected onto the exterior surface of the object. The illumination area on the exterior surface of the object may indicate where the cutting edge 132 of the blade 103 will contact the exterior surface so as to make the dermaplaning experience easier for the user. The light guide 154 may also illuminate at least a side of the blade 103, a region surrounding the blade 103, or any combination thereof.

As illustrated in FIG. 10, a power source 105 may be in electric communication with the light source of the lighting arrangement 124 and/or lighting arrangement 130. The power source 105 may be one of a rechargeable battery, a disposable battery, or any other type of power storage mechanism. In some example embodiments, and as illustrated in FIG. 10, the power source 105 may be arranged about the second end 118 of the handle 102, although other arrangements of the power source 105 are also contemplated. For example, the second end 118 of the handle 102 may define an internal compartment or cavity 129, as illustrated in FIG. 10, that is arranged to contain the power source 105 therein. A rear cover may be removably attached to the second end 118 of the handle 102 so as to cover the internal compartment or cavity 129. As such, the power source 105 may be removable from the internal compartment 129 through removal of the rear cover, or the power source 105 may remain within the internal compartment 129 and may be rechargeable. A seal, gasket, or other device to prevent moisture and humidity from entering the internal compartment 129 may be provided about the second end 118 of the handle 102, as well.

The lighting arrangement 124 and/or the lighting arrangement 130 may comprise a translucent material, a transparent material, or any other type of material that allows light to pass through. In order to facilitate usage of the lighting arrangement 124 of the dermaplaning device 100, in some example embodiments, the blade assembly 110 (i.e., the structure) may comprise a translucent material such that light from the light source of the lighting arrangement 124 may pass through the translucent material of the blade assembly 110 so as to illuminate at least a portion of the blade assembly 110 and thereby a target area during use of the dermaplaning device 100. Alternatively, the blade assembly 110 may comprise a transparent material, or any other type of material that allows light to pass through the blade assembly 110. However, the dermaplaning device 100 is still usable without the lighting arrangement 124 and/or lighting arrangement 130 and the blade 103 may still be utilized to scrape against the exterior surface of the object without the lighting arrangement 124 and/or lighting arrangement 130 providing illumination. It is advantageous to use the lighting arrangement 124 and/or lighting arrangement 130, though, in order to illuminate a region on the exterior surface of the object to be dermaplaned and thus allow for more precise usage of the dermaplaning device 100.

In some example embodiments, the dermaplaning device 100 may comprise a charging system (not shown) for charging the power source 105, where the power source 105 is a rechargeable power storage device (e.g., rechargeable battery). The charging system may receive energy through motion, an electrical connection, light, induction, a magnetic field, radiofrequency, or other wireless means. For example, the charging system may include a cable that is insertable through a port 170 (FIG. 13) defined in the device 100 and electrically connected to the power source 105 and an external power source, such as a wall socket.

A switch or power button 123 may be provided on the handle 102. The switch 123 may be depressible or otherwise actuatable. The switch 123 may be in electric communication with the power source 105, and may be arranged to activate the power source 105 and thereby illuminate at least a portion of the blade assembly 110 when actuated and/or transmit power to the blade assembly 110 and/or blade 103. More particularly, and as illustrated in FIG. 10, the switch 123, the power source 105, and the lighting arrangement 124 and/or lighting arrangement 130 may be connected together with a circuit board (e.g., a printed circuit board) 128, such that when the switch 123 is activated the formed circuit is completed and electricity is flowable from the power source 105 to the lighting arrangement 124 and/or lighting arrangement 130. In some example embodiments, and as illustrated in FIGS. 11 and 15, contacts or wires 127 may pass from the power source 105 to the blade assembly 110 and/or the blade 103 so as to provide power to the blade assembly 110.

In some example embodiments, a motor 106 may be in electric communication with the power source 105 and the blade 103, wherein the motor 106 is configured to cause one or both of vibration and reciprocation of the blade 103 upon actuation of the motor 106. More particularly, the switch 123, the power source 105, the blade 103, the motor 106, the lighting arrangement 124 and/or lighting arrangement 130 may form a circuit, such that when the switch 123 is activated the circuit is completed and electricity is flowable from the power source 105 to the motor 106 so as to cause the blade 103 to move, and/or the lighting arrangement 124 and/or lighting arrangement 130 to illuminate the region on the exterior surface of the object. The motor 106 may use an off-center mass to create vibration based on momentum of the off-center mass. Vibration generation can also be accomplished by a piezoelectric or magnetic vibrator, rather than a rotary motor. The motor 106 may have different settings, so that different vibrational or reciprocating speeds and patterns may cause the blade 103 to move differently in response thereto. The different settings may be desirable where, for example, different types of hair or skin are being scraped with the blade 103 and require different amounts of scraping force.

In some example embodiments, a sensor mechanism may be incorporated with the circuit. The sensor mechanism may be a type of mechanism that is able to determine if the user is using the device 100 correctly, e.g., is applying enough pressure, user is holding the device at the desired angle, etc. The sensor mechanism may be a gyroscope, an accelerometer, pressure sensors, electrical conductivity sensors, optical sensors, force sensors, or combinations thereof. Feedback may be reported to the user via different colored lights, vibrations, and the like. For example, the sensor mechanism may be configured to detect whether the dermaplaning device 100 is being held, and as a result, output a signal to an indicator 126 (FIGS. 15 and 16), the lighting arrangement 124 and/or lighting arrangement 130 to automatically provide illumination. In another example, and as illustrated in FIGS. 19 and 20, the sensor mechanism may be a strip of conductive material 156, which may be arranged on either side of the recess 121. The conductive material 156 may be positioned to make contact with the exterior surface (e.g., skin) only when the blade 103 is positioned at a predetermined, optimal angle (e.g., 15 degrees). When the strip of conductive material 156 comes into contact with the exterior surface, a capacitive sensor electrically connected to the conductive material 156 may output a signal to the indicator 126, lighting arrangement 124 and/or lighting arrangement 130 to provide illumination so as to provide feedback to the user that the dermaplaning device 100 is being held at the optimal angle.

In some example embodiments, an icon (not shown) may be illuminated based on a state of the dermaplaning device 100 and/or certain actions of the user. For example, the icon may be in electrical communication with the sensor mechanism and become illuminated in response to an output from the sensor mechanism. In this example, the sensor mechanism may be a pressure sensor that measures the contact pressure between the exterior surface of the object and the device 100 and outputs a signal to the lighting arrangement 124 and/or lighting arrangement 130 to illuminate the icon if the contact pressure applied corresponds to a pre-determined amount. In another example, the sensor mechanism may be a capacitive sensor that measures the angle at which the user is holding the device 100 and outputs a signal to the lighting arrangement 124 to illuminate the icon if the angle corresponds to a pre-determined angle of use. In some example embodiments, the light output may be different colors in either example depending on the signal. A red light may illuminate the icon if the angle or contact pressure does not correspond to the pre-determined amount, and a green light may illuminate the icon if the angle or contact pressure corresponds to the pre-determined amount.

Referring to FIG. 12, a cover 107 may be arrangeable about the first end 117 of the handle 102 so as to enclose at least the cutting edge 132 of the blade 103. The cover 107 may be a translucent material, a transparent material, or any combination thereof so that a user can see through the cover to ascertain whether a blade 103 is attached to the blade assembly 110. As illustrated in FIG. 12, for example, the cover 107 extends over the blade assembly 110 and the blade 103, but not the first end 117 of the handle 102. In some example embodiments, the blade assembly 110 may not be removable from the handle 102 without the cover 107 enclosing at least the cutting edge 132 of the blade 103.

Referring now to FIGS. 21-22, a blade dispenser 104 is illustrated. The blade dispenser 104 may be a component or element of a dermaplaning system that includes a dermaplaning device, such as the dermaplaning device 100. The blade dispenser 104 may define a plurality of cavities 141, each cavity 141 being arranged to retain a blade assembly 110 including a blade 103 therein and dispense the blade assembly 110 upon engagement of the top side of the blade assembly 110 with the recess 121 of the dermaplaning device 100. In this manner, a user may change blade assemblies 110 without having to directly contact the blade assemblies 110, and thereby the blade 103. In some example embodiments, the cavities 141 are arranged to fan out, although in other example embodiments the cavities 141 are arranged parallel to one another, are in staggered formation relative to one another, etc. As illustrated in FIGS. 21 and 22, the cavities are arranged parallel to one another and a blade 103 is received in each of the cavities 141.

To remove a blade assembly 110 from one of the cavities 141 in the blade dispenser 104, the dermaplaning device 100 may be brought into alignment with the blade assembly 110 retained in the blade dispenser 104 so that the top side of the dermaplaning device 100 is brought into engagement with the recess 121. Once engagement between these elements occurs, the dermaplaning device 100 may be lifted away from the blade dispenser 104 so that cavities 141 of the blade dispenser 104 release the blade assembly 110.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. A derma planing device comprising:
a longitudinally-extending handle having a first end defining a longitudinally-extending recess extending externally to the handle and along a length of the first end and an opposing second end;
a blade assembly having a top side engageable with the recess of the handle and an opposing bottom side comprising a blade with a cutting edge;
a lighting arrangement provided about the first end of the handle to illuminate at least a portion of the blade assembly engaged with the recess, the lighting arrangement comprising a light source in electric communication with a power source; and
a safety guard arranged over the cutting edge of the blade so as to limit a cutting depth of the blade;
wherein the blade assembly comprises a translucent material such that light from the light source passes through the translucent material of the blade assembly so as to illuminate the at least a portion of the blade assembly engaged with the recess and thereby illuminate a target area during use of the derma planing device.

2. The device of claim 1, further comprising a switch in electric communication with the power source, the switch being arranged to activate the power source and thereby illuminate at least a portion of the blade assembly when actuated.

3. The device of claim 1, wherein the light source is arranged on the first end of the handle and adjacent to the recess.

4. The device of claim 1, wherein the second end of the handle defines an internal compartment arranged to contain the power source.

5. The device of claim 1, further comprising a motor in electric communication with the power source and the blade, wherein the motor is configured to cause one or both of vibration and reciprocation of the blade upon actuation of the motor.

6. The device of claim 1, wherein the blade assembly is attachable to and removable from the first end of the handle.

7. The device of claim 1, further comprising a cover arrangeable about the first end of the handle so as to enclose at least the cutting edge of the blade.

8. The device of claim 1, wherein the blade assembly and the handle are engageable by magnets, a press fit, a snap fit, a twist lock, a biased lock, or combinations thereof.

9. The device of claim 1, further comprising an ejection button disposed on the handle, wherein actuation of the ejection button releases the blade assembly including the blade from engagement with the recess of the handle.

10. The device of claim 1, wherein the first end of the handle defining the recess is longitudinally offset from the opposing second end of the handle.

11. The device of claim 1, wherein the second end of the handle comprises a gripping region for a user to grip the dermaplaning device during use.

12. A dermaplaning system comprising:
a derma planing device comprising:
a longitudinally-extending handle having a first end defining a longitudinally-extending recess extending externally to the handle and along a length of the first end and an opposing second end;
a blade assembly having a top side engageable with the recess of the handle and an opposing bottom side comprising a blade with a cutting edge;
a lighting arrangement provided about the first end of the handle to illuminate at least a portion of the blade assembly engaged with the recess, the lighting arrangement comprising a light source in electric communication with a power source;
a safety guard is arranged over the cutting edge of the blade so as to limit a cutting depth of the blade;
wherein the blade assembly comprises a translucent material such that light from the light source passes through the translucent material of the blade assembly so as to illuminate the at least a portion of the blade assembly engaged with the recess and thereby illuminate a target area during use of the derma planing device; and
a blade dispenser defining a plurality of cavities, each cavity being arranged to retain a blade therein and dispense the blade upon engagement of the top side of the blade with the recess of the derma planing device.

13. The system of claim 12, wherein the dermaplaning device comprises a switch in electric communication with the power source, the switch being arranged to activate the power source and thereby illuminate at least a portion of the blade assembly when actuated.

14. The system of claim 12, wherein the light source is arranged on the first end of the handle and adjacent to the recess.

15. The system of claim 12, wherein the dermaplaning device comprises a motor in electric communication with the power source and the blade, wherein the motor is configured to cause one or both of vibration and reciprocation of the blade upon actuation of the motor.

* * * * *